United States Patent [19]

Kojima et al.

[11] Patent Number: 4,942,242

[45] Date of Patent: Jul. 17, 1990

[54] CERTAIN THIAZOL-4-YL-PHENOXY DERIVATIVES HAVING LIPID LOWERING PROPERTIES

[76] Inventors: Tadao Kojima, No. 1086-2, Minamisaitama-gun, Saitama; Shunji Kageyama, No. 1-36-6, Nakano, Nakano-ku, Tokyo; Minoru Okada, No. 6-10-20, Higashioi, Shinagawa-ku, Tokyo; Isao Ohata, No. 47-17, Omiya-shi, Saitama; Noboru Sato, No. 3-180-1, Nishimiyashita, Ageo-shi, Saitama, all of Japan

[21] Appl. No.: 261,552

[22] Filed: Oct. 21, 1988

Related U.S. Application Data

[60] Division of Ser. No. 203, Jan. 2, 1987, Pat. No. 4,794,113, which is a continuation-in-part of Ser. No. 623,174, Jun. 21, 1984, abandoned.

[30] Foreign Application Priority Data

Jun. 24, 1983 [JP] Japan ................................. 58-113988

Oct. 27, 1983 [JP] Japan ......................... 58-201639

[51] Int. Cl.$^5$ .................. C07D 277/32; C07D 277/42; C07D 277/44; C07D 277/54

[52] U.S. Cl. .................................... 548/192; 548/194; 548/195; 548/204; 548/205; 546/280; 546/291

[58] Field of Search ............... 548/341, 204, 205, 192, 548/194, 195

[56] References Cited

U.S. PATENT DOCUMENTS 4,794,113 12/1988 Kojima et al. ...................... 514/399
4,795,753 1/1989 Kojima et al. ...................... 514/345

*Primary Examiner*—Alan L. Rotman
*Attorney, Agent, or Firm*—Burgess, Ryan & Wayne

[57] ABSTRACT

Thiazolyl phenoxy derivatives are provided as well as pharmaceutical compositions containing such derivatives. The compositions are useful for lowering lipid activity in a subject and accordingly useful for reducing cholesterol and triglycerides.

10 Claims, No Drawings

CERTAIN THIAZOL-4-YL-PHENOXY DERIVATIVES HAVING LIPID LOWERING PROPERTIES

This is a division of Ser. No. 000,203, filed Jan. 2, 1987, now U.S. Pat. No. 4,794,113, which is a continuation-in-part of U.S. Ser. No. 623,174, filed 6/21/84, now abandoned.

The present invention relates to novel phenoxy derivatives represented by the formula (I):

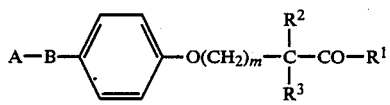

wherein:
A is a 1-imidazolyl group, a pyridyl group, a pyridyloxy group, an oxo-substituted chromenyloxy group, a lower alkyl group, an amino group which may be substituted with a phenyl group or a lower alkyl group, or a carbamoyl group substituted with a cyclohexylamino group or an imidazolylalkyl group;
B is a single bond, a thiazolyl group which may be substituted with a lower alkyl group, a group represented by the formula:

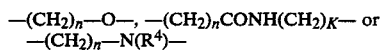

wherein:
K is 0 or an integer of 1 to 5,
n is an integer of 1 to 6 and
$R^4$ is hydrogen or a lower alkyl group;
m is 0 or an integer of 1 to 6;
$R^1$ is a hydroxyl group, an amino group or a lower alkoxy group;
$R^2$ and $R^3$, which may be the same or different, represent a hydrogen atom or a lower alkyl group hereafter the same:
and salts thereof.

In the definition of the groups appearing in the formulae in the specification, the term "lower" refers to a straight or branched carbon chain having 1 to 5 carbon atoms, preferably 1 to 3 carbon atoms. Accordingly, specific examples of lower alkyl groups include a methyl group, an ethyl group, a propyl group, an isopropyl group, a butyl group, an isobutyl group, a sec-butyl group, a tert-butyl group, a pentyl (or amyl) group, an isopentyl group, a neopentyl group, a tert-pentyl group, etc.

The compounds represented by the general formula (I) described above form salts thereof, and in particular, salts which are acceptable for pharmaceutical use. In particular, preferred salts include the pharmaceutically acceptable salts with inorganic acids such as hydrochloric acid, hydrobromic acid, phosphoric acid, etc.; pharmaceutically acceptable salts with organic acids such as formic acid, acetic acid, lactic acid, oxalic acid, succinic acid, fumaric acid, benzoic acid, benzenesulfonic acid, etc.; and other salts such as quaternary ammonium salts with alkyl halides such as methyl iodide, etc.

Further, the compounds of the present invention also include compounds in which geometric isomers and a variety of optical isomers (racemic isomers and optically active isomers, etc.) exist and the present invention cover all of these isomers.

The desired compounds of the present invention possess lipid lowering activity, particularly excellent activity for reducing cholesterol and triglyceride and at the same time, also possess an activity for preventing platelet aggregation. The compounds of the present invention are effective for prophylaxis and treatment of arteriosclerosis, cerebral infarction, transient ischemic attack, angina pectoris, peripheral thrombus and obstruction.

According to animal tests, it is recognized that the compounds of the present invention possess excellent activity for reducing cholesterol and triglycerides and an activity for selectively increasing high density lipoprotein (HDL) in blood. It is known with HDL that the quantity of HDL decreases in arterioscrelosis as compared to normal state; HDL prevents excessive accumulation of cholesterol in the arterial wall and HDL accelerates the release of cholesterol from the arterial wall to Blood. In addition, the compounds of the present invention possess an activity of preventing platelet aggregation induced by arachidonic acid. This activity is combined with lipid reducing activity to contribute to prophylaxis and treatment of the aforesaid various diseases such as arteriosclerosis, etc.

The pharmacological effects of the compounds of the present invention have been confirmed as follows:

Lipid Reducing Activity:

Feed containing 1.5% cholesterol and 0.5% bile acid was given to male Sprague-Dawley rats aging 4 weeks old after birth for 7 days. A suspension of the compound of the present invention in a 0.5% aqueous methyl cellulose solution was administered daily via oral catheter for 4 days. After fastening overnight, blood was collected under ether anesthesia to determine the quantities of the total HDL and cholesterol in serum. The measurements of cholesterol and HDL were performed in accordance with the method described in Schettler, G. & Hüssel; *Arbetsmed. Sozialmed. Praventived.*, 10, 25 (1975) and the method described in T. T. Ishikawa et al.; *Lipids*, 11, 628 (1976), respectively. The lipid reducing activity of representative compounds of the present invention is shown in Table I below.

Platelet Aggregation Prevention Activity:

Platelet rich plasma (PRP) and platelet poor plasma (PPP) were prepared from venous blood of Nippon white rabbit. The platelet aggregation activity was measured in accordance with the method described in Born, G. V. R.; *Nature*, 194, 927 (1962) and the activity of preventing platelet agglutination of the compound against platelet aggregation induced by arachidonic acid (final concentration, 0.2 mM) was determined with an Aggrigometer (made by Payton Co.).

The platelet aggregation inhibitory activity of representative compounds of the present invention is shown in Table I.

TABLE I

| Structural Formula | Dose p.o. (mg/kg/day) | Hyperlipedemic rat Reduction Rate of T* and Chol** (%) | HDL-Chol** cont. = 1 | HDL-C LDL-C cont. = 1 | Platelet Aggregation inhibition (%) A.A. |
|---|---|---|---|---|---|
| Example 2: (pyridyl-C(=S)-N=CH-C6H4-O(CH2)5C(CH3)2-COOC2H5) | 100 | 59 | 7.62 | 22 | 100 μM 16 |
| Example 5: (CH3-C(=S)-N=CH-C6H4-O(CH2)3C(CH3)2-COOC2H5) | 100 | 69 | 1.54 | 8.00 | 100 μM 50 |
| Example 30: (imidazolyl-N-(CH2)3O-C6H4-O(CH2)4C(CH3)2-COOC2H5) | 100 | 48 | 1.78 | 5.00 | 100 μM 57 |
| Example 35: (imidazolyl-N-(CH2)3CONH-C6H4-O(CH2)4C(CH3)2-COOC2H5) | 100 | 52 | 2.49 | 5.4 | 100 μM 7 |
| Example 39: (imidazolyl-N-(CH2)4CONH-C6H4-O(CH2)5C(CH3)2-COOC2H5) | 100 | 23 | 3.11 | 4.1 | 100 μM 100 |

*triglyceride
**cholesterol

Drugs containing the compounds represented by general formula (I) or salts thereof as active ingredients can be prepared using pharmaceutical carriers, vehicles conventionally used in the art in a conventional manner.

Mode of administration may be oral administration in the form of powders, granuels, capsules or parenteral administration such as injection, etc. but preferably administered orally.

The dosage can be appropriately determined depending upon conditions, age and sex, etc., of the patient to be administered; however, in the case of oral administration, the dose may be in the range of 1 to 100 mg/kg daily for adults, preferably 5 to 25 mg/kg, which may be given once or divided into 2 to 4 times.

According to the present invention, the compounds (I) of the present invention and salts thereof can be prepared by the methods illustratively shown below.

Method A $$D-C(=S)NH_2 + \text{(II)}$$

-continued

Method A

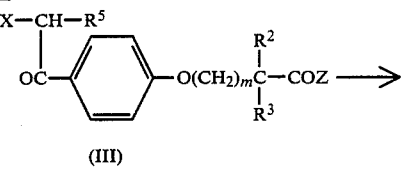

(III)

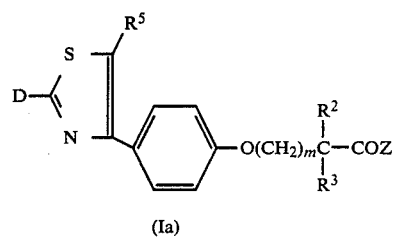

(Ia)

wherein Z represents an amino group or a group represented by formula $-OR^{1'}$ (wherein $R^{1'}$ is a hydrogen atom, a lower alkyl group or a protective group), D represents an imidazolyl group, a pyridyl group, a lower alkyl group, or an amino group which may be substituted with a phenyl group or a lower alkyl group; $R^5$ represents a hydrogen atom or a lower alkyl group;

X represents a halogen atom and $R^2$, $R^3$ and m have the same significance as defined above.

To prepare the compounds of the present invention according to Method A, the thioamide compound represented by formula (II) and ω-(halogenoacetylphenoxy)alkyl carboxylic acids or esters thereof (III) are reacted in a solvent inert to the reaction.

Preferred examples of the solvents include acetone, alcoholic solvents such as methanol, ethanol, etc. The proportion of compounds (II) to compounds (III) to be used is almost equimolar.

The reaction easily proceeds at room temperature but if necessary and desired, heating is performed.

The thus obtained compounds can be converted to salts thereof, if necessary, by reacting with the aforesaid acids or bases. Further in case that the desired compounds are free acids, the acids can be converted to esters thereof in a conventional manner.

Further in case that D is a free amino group, cycloalkyl isocyanates or imidazolylalkylcarboxylic acids can be reacted with the compounds represented by formula (Ia). In the case of reacting with cycloalkyl isocyanates, the reaction is conducted under reflux using tetrahydrofuran, etc. as a solvent. In the case of reacting with imidazolylalkylcarboxylic acids, the reaction is performed with heating in N,N-dimethylformamide (hereafter referred to as DMF) in the presence of dicylohexylcarbodiimide (hereafter referred to as DCC).

Method B

E—(CH$_2$)$_n$—COOH or reactive derivatives thereof +

(IV)

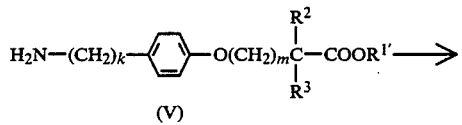

(V)

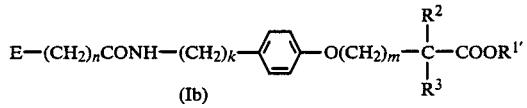

(Ib)

wherein E represents an imidazolyl group or a pyridyloxy group, represents an integer of 1 to 6 and, $R^{1'}$, $R^2$, $R^3$, m and k have the same significance as defined above.

To prepare the compounds of the present invention according to Method B, the carboxyl compounds represented by formula (IV) or reactive derivatives thereof are reacted with the amino compounds represented by formula (V).

Typical examples of the reactive derivatives of compounds (IV) include acid halides such as acid chlorides, acid bromides, etc.; acid azides; active esters such as N-hydroxybenztriazole esters, p-nitrophenyl esters, p-chlorophenyl esters, etc.; symmetric acid anhydrides; mixed acid anhydrides such as alkyl carbonate mixed acid anhydrides obtained by reacting alkyl carbonate halides, e.g., isobutyl carbonate chloride, methyl carbonate chloride, ethyl carbonate bromide, etc. with compounds (IV), and the like.

In case that compounds (IV) are reacted in the form of free carboxylic acids, the reaction is advantageously conducted in the presence of a condensing agent such as N,N'-dicyclohexylcarbodiimide, 1,1-carbonyldiimidazole, etc.

In case that the reactive derivatives are reacted, it is often advantageous that the reaction is carried out in the presence of tertiary bases such as triethyl amine, pyridine, picoline, rutidine, N,N-dimethylaniline, etc. or in the presence of bases such as potassium carbonate, sodium carbonate, sodium hydroxide, potassium hydroxide, etc., whereby the reaction can be accelerated.

Solvents, temperature conditions and the like can be appropriately chosen depending upon the kind of the reactive derivatives used, etc. Examples of the solvents ordinarily used include organic solvents such as pyridine, benzene, toluene, dimethylformamide, dioxan, ether, tetrahydrofuran, chloroform, dichloromethane, dichloroethane, etc., or a mixture thereof.

Method C

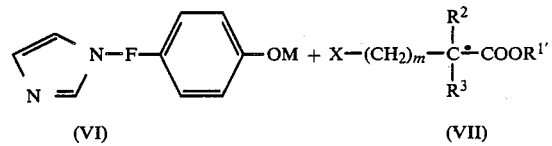

(VI)                              (VII)

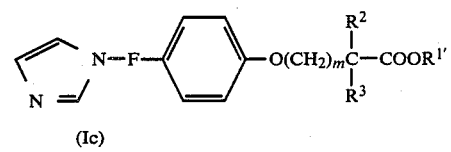

(Ic)

wherein F represents a single bond, a group represented by the formulae: —(CH$_2$)$_n$CONH—, —(CH$_2$)$_n$—O— or —(CH$_2$)$_n$—N(R$^4$)—, M represents a hydrogen atom or an alkali metal, $R^{1'}$, $R^2$, $R^3$, X, n and m have the same significance as defined above.

Among the compounds of the present invention, the ether compounds represented by general formula (Ic) can be prepared by reacting the corresponding phenol compounds (VI, M=H) with the alkyl halides represented by general formula (VII) either in the presence of bases or as alkali metal phenoxides (VI, M=alkali metal).

As halogen atoms, an iodine atom, a bromine atom, a chlorine atom, etc. are preferred and sodium and potassium are preferred as alkali metals.

It is advantageous that the reaction be carried out at room temperature or with heating under reflux in organic solvents inert to the reaction, such as alcohols, e.g., methanol ethanol, etc.; dimethyl sulfoxide, DMF, benzene, toluene, xylene, ether, tetrahydrofuran, etc.

Preferred examples of bases include potassium carbonate, sodium amide, sodium hydroxide, etc.

Method D

G—M +

(VIII)

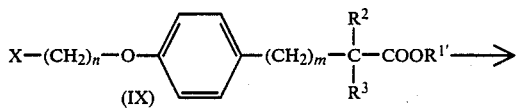

(IX)

Method D

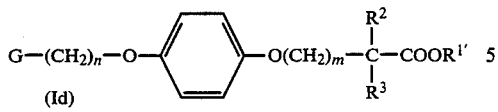
(Id)

wherein G represents an imidazolyl group, a pyridyloxy group or an oxo-substituted chromenyloxy group, $R^{1'}$, X, n, m, M, $R^3$ and $R^2$ have the same significance as defined above.

To prepare the compounds of the present invention, compounds (VIII, M=H) having an imidazolyl group, a pyridyloxy group or an oxo-substituted chromenyloxy group are reacted with halogen compounds represented by general formula (IX) in the presence of bases or the alkali metal salts thereof (VIII, M=alkali metal) reacted with halogen compounds.

The reaction is advantageously carried out at room temperature or with heating in organic solvents inert to the reaction, such as dimethyl sulfoxide, DMF, benzene, toluene, xylene, ether, tetrahydrofuran, etc.

Preferred examples of bases which can be used include alkali metal hydrides such as sodium hydride, alkali methal alcoholates such as sodium ethoxide, organic lithium compounds such as n-butyl lithium, etc.

Examples of the protective group used in said Methods A - B are optionally substituted benzyl group, a trityl group, an alkyloxyalkyl group, a phenacyl group, etc.

Further, in case that $R^{1'}$ in said formulae Ia, Ib, Ic or Id is a lower alkyl group or a protective group, the group may optionally be removed in a conventional manner.

The compounds of the present invention prepared by the various methods as described above are isolated as they are or as the salts and purified. Isolation and purification are performed in a conventional manner in the art such as crystallization, distillation, extraction, various chromatography techniques, recrystallization, etc.

Hereafter the present invention will be described in more detail with reference to the examples. Some of the starting compounds of the present invention are novel and preparation of such compounds is shown in the reference examples below.

REFERENCE EXAMPLE 1

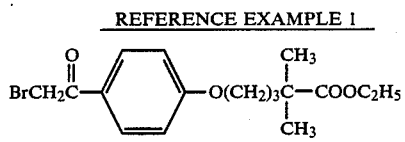

A mixture of 30 g of p-hydroxyacetophenone and 30 g of potassium carbonate was stirred in 500 ml of ethanol at 60° C. for 30 minutes. After cooling to room temperature, 52 g of ethyl 5-bromo-2,2-dimethylpentanoate was added to the reaction mixture. The resulting mixture was heated under reflux overnight while stirring. The solvent was removed from the reaction mixture by distillation and, 500 ml of chloroform and 300 ml of a 5% aqueous hydrogen sodium carbonate solution were added to the residue. After stirring the mixture, the chloroform layer was fractionated and washed successively with water and then with a saturated aqueous sodium chloride solution followed by drying over anhydrous sodium sulfate. Removal of chloroform by distillation gave a residual oily substance. The oily substance was subjected to silica gel column chromatography and eluted using chloroform as an eluant to give 42 g of ethyl p-acetylphenoxy-2,2-dimethylpentanoate as an oily substance. The thus obtained oily substance was dissolved in 1.6 l. of anhydrous methylene chloride and 24 g of bromine was dropwise added to the solution under ice cooling while stirring to allow to react for 3 hours. To the reaction mixture was added 1 liter of ice water. After thoroughly stirring, the organic layer was successively washed with water and with a saturated aqueous sodium chloride solution followed by drying over anhydrous sodium sulfate. Removal of methylene chloride by distillation gave the desired product, ethyl 5-[p-(bromoacetyl)-phenoxy]-2,2-dimethylpentanoate, as an oily substance.

REFERENCE EXAMPLE 2

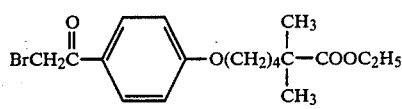

Ethyl 6-bromo-2,2-dimethylhexanoate was used as the starting material in place of ethyl 5-bromo-2,2-dimethylpentanoate in REFERENCE EXAMPLE 1. The starting material was reacted and treated in a manner similar to REFERENCE EXAMPLE 1 to give the desired product, ethyl 6-[p-bromoacetylphenoxy]-2,2-dimethylhexanoate as an oily substance.

REFERENCE EXAMPLE 3

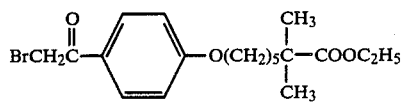

Ethyl 7-bromo-2,2-dimethylheptanoate was used as the starting material in place of ethyl 5-bromo-2,2-dimethylpentanoate in REFERENCE EXAMPLE 1. The starting material was reacted and treated in a manner similar to REFERENCE EXAMPLE 1 to give the desired product, ethyl 7-[p-bromoacetylphenoxy]-2,2-dimethylheptanoate as an oily substance.

REFERENCE EXAMPLE 4

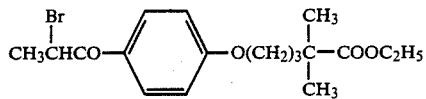

p-Hydroxypropiophenone was used as the starting material in place of p-hydroxyacetophenone in REFERENCE EXAMPLE 1. The starting material was reacted and treated in a manner similar to REFERENCE EXAMPLE 1 to give the desired product, ethyl 5-[p-(2-bromopropionyl)phenoxy]-2,2-dimethylpentanoate as an oily substance.

REFERENCE EXAMPLE 5

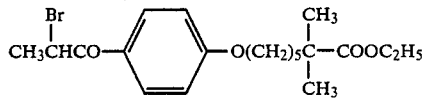

p-Hydroxypropiophenone was used as the starting material in place of p-hydroxacetophenone in REFERENCE EXAMPLE 3. The starting material was reacted and treated in a manner similar to REFERENCE EXAMPLE 3 to give the desired product, ethyl 7-[p-(2-bromopropionyl)phenoxy]-2,2-dimethylheptanoate as an oily substance.

REFERENCE EXAMPLE 6

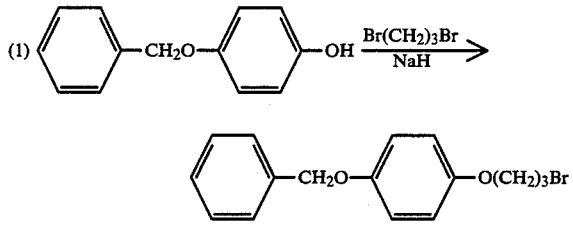

After 5.0 g of sodium hydride (60% suspension in a mineral oil) was washed with dry benzene, 100 ml of dry N,N-dimethylformamide was added thereto. While stirring at room temperature, 25 g of hydroquinone-mono benzyl ether was added to the mixture. After vigorous bubbling was over, the resulting suspension was heated at 80° C. for 30 minutes while stirring and then cooled to room temperature. A solution of 75 ml of dibromopropane in 40 ml of dry N,N-dimethylformamide was added to the suspension; heating was conducted at 60° C. for 4 hours while stirring. The solvent was removed from the reaction mixture by distillation under reduced pressure. The residue was dissolved in methylene chloride and the solution was successively washed with a 5% aqueous hydrogen sodium carbonate solution, water and then a saturated aqueous sodium chloride solution followed by drying over anhydrous sodium sulfate. After drying, the solvent was distilled off under reduced pressure. The residual oily substance was subjected to silica gel column chromatography and the desired product was eluted using a benzene-n-hexane mixture (2:3) as an eluant. The solvent was removed from the eluate by distillation under reduced pressure to give the desired product, p-(3-bromopropoxy)phenyl benzyl ether, as an oily substance.

NMR Spectrum (CDCl$_3$) (internal standard: TMS)δ(ppm): 1.9 (quint, 2H, —C—CH$_2$—C—, J=7.2 Hz) 3.4 (t, 2H, Br—CH$_2$—C—, J=7.2 Hz)

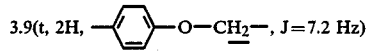

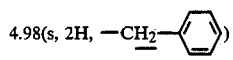

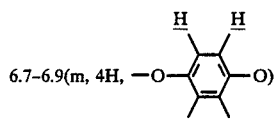

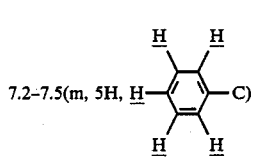

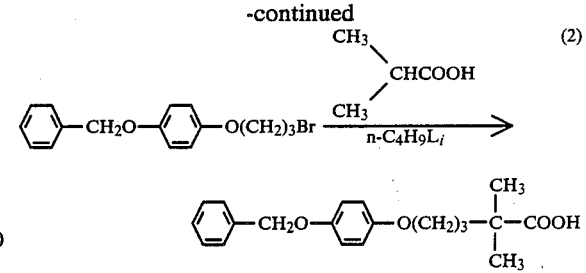

To a solution of 15 g of diisopropylamine in 75 ml of dry tetrahydrofuran was dropwise added 100 ml of n-butyl lithium (15 w/w, n-hexane solution) at −5° to 0° C. After stirring at the same temperature for 30 minutes, 6.7 g of isobutyric acid was added dropwise to the mixture. After stirring was continued at the same temperature for 1 hour, a solution of 20 g of p-(3-bromopropoxy)phenyl benzyl ether in 60 ml of dry tetrahydrofuran was added dropwise to the solution. Thirty minutes after, the mixture was stirred at room temperature for 16 hours. The mixture was cooled and 250 ml of water was added thereto. After the aqueous layer was washed with ether, the aqueous layer was acidified with 6N hydrochloric acid and extracted twice with 70 ml of methylene chloride. The extract was washed with an aqueous saturated sodium chloride solution and then dried over anhydrous sodium sulfate. After drying, the solvent was removed by distillation under reduced pressure and the residue was recrystallized from ethyl acetate to give the desired product, 5-(p-benzyloxyphenoxy)-2,2-dimethylpentanoic acid.

Melting point: 112°–113° C.

| Elemental Analysis (as $C_{20}H_{24}O_4$) | | |
| --- | --- | --- |
| | C (%) | H (%) |
| Calcd. | 73.15 | 7.37 |
| Found | 73.34 | 7.40 |

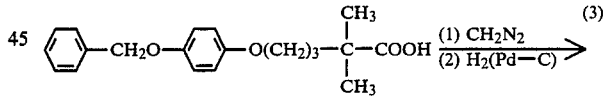

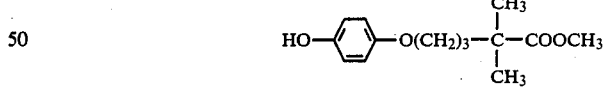

In 100 ml of tetrahydrofuran was dissolved 9 g of 5-(p-benzyloxyphenoxy)-2,2-dimethylpentanoic acid. The resulting solution was treated with a diazomethane-ether solution in a conventional manner to give methyl 5-(p-benzyloxyphenyloxy)-2,2-dimethylpentanoate.

The thus obtained ester was dissolved in 200 ml of methanol and 10% palladium-carbon was added to the solution. The mixture was reacted with stirring in a hydrogen atmosphere under normal pressure until a theoretical amount of hydrogen was absorbed. Palladium-carbon was removed by filtration and the solvent was removed by distillation under reduced pressure to give the desired product, methyl 5-(p-hydroxyphenoxy)-2,2-dimethylpentanoate as crystals.

Melting point: 53°–54° C.

| Elemental Analysis (as $C_{14}H_{20}O_4$) | | |
|---|---|---|
| | C (%) | H (%) |
| Calcd. | 66.65 | 7.99 |
| Found | 66.53 | 8.01 |

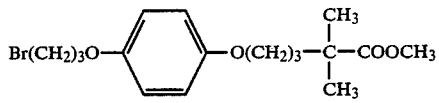
(4)

Methyl 5-(p-hydroxyphenoxy)-2,2-dimethylpentanoate was used as the starting material in place of hydroquinone-mono benzyl ether in REFERENCE EXAMPLE 6 (1). The starting material was reacted and treated in a manner similar to REFERENCE EXAMPLE 6 (1) to give the desired product, methyl 5-[p-(3-bromopropoxy)phenoxy]-2,2-dimethylpentanoate as an oily substance.

NMR Spectrum ($CDCl_3$) (internal standard: TMS)
δ (ppm)

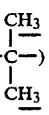
1.18(s, 6H, 1.4–2.0(m, 4H, Br—C—$\underline{CH_2}$—C—, O—C—$\underline{CH_2}$—C)

2.0–2.3(m, 2H, 3.58(t, 2H, Br—$\underline{CH_2}$—, J=6.5 Hz)

3.62(s, 3H, $\underline{CH_3}$OOC—)

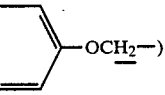
3.7–4.0(m, 4H, —$\underline{CH_2}$—O—⟨⟩—O$\underline{CH_2}$—)

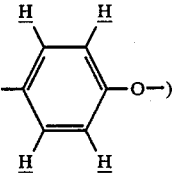
6.76 (s, 4H, —O—⟨⟩—O—)

REFERENCE EXAMPLE 7

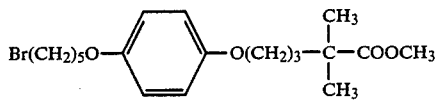

To 2.52 g of methyl 5-(p-hydroxyphenoxy)-2,2-dimethylpentanoate and 1.38 g of anhydrous potassium carbonate was added 30 ml of ethanol and the mixture was heated under reflux for 30 minutes while stirring. After cooling, 2.53 g of 1,5-dibromopentane was added thereto and the mixture was reacted overnight with heating under reflux. After the solvent was removed by distillation under reduced pressure, water was added to the resulting residue followed by extracting with chloroform. After the chloroform layer was successively washed with an aqueous saturated hydrogen sodium carbonate solution and then an aqueous saturated sodium chloride solution, the chloroform layer was dried over anhydrous sodium sulfate. The solvent was removed by distillation under reduced pressure and the resulting residue was subjected to silica gel column chromatography. The product was eluted using an n-hexane-ethyl acetate mixture (8:1 in a volume ratio). The solvent was removed by distillation to give the desired product, methyl 5-[p-(5-bromopentyloxy)phenoxy]-2,2-dimethylpentanoate as an oily substance.

REFERENCE EXAMPLE 8

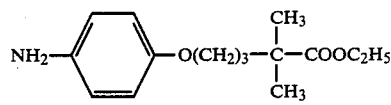

In 40 ml of ethanol were dissolved 3.22 g of sodium p-nitrophenol and 4.74 g of ethyl 5-bromo-2,2-dimethylpentanoate and the solution was allowed to react with heating under reflux for 24 hours.

The solvent was removed by distillation under reduced pressure and ice water was added to the residue followed by extracting with chloroform. After the chloroform layer was washed with water, the chloroform layer was dried over anhydrous sodium sulfate. The solvent was removed by distillation under reduced pressure to give ethyl 5-(p-nitrophenoxy)-2,2-dimethylpentanoate as an oily substance. The oily substance was dissolved in 100 ml of ethanol and 0.3 g of 5% palladium-carbon was added to the solution. The reaction was then performed with stirring in a hydrogen atmosphere under normal pressure until a theoretical amount of hydrogen was absorbed.

After palladium-carbon was removed by filtration, the solvent was removed by distillation under reduced pressure and the residue was subjected to silica gel column chromatography. The product was eluted using a chloroform-methanol mixture (100:1 ratio) in a volume as an eluant. The solvent was removed from the eluate by distillation under reduced pressure to obtain ethyl 5-(p-aminophenoxy)-2,2-dimethylpentanoate as an oily substance.

REFERENCE EXAMPLES 9 AND 10

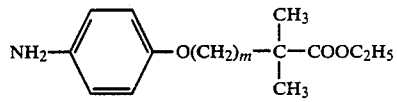

A compound having the above formula wherein m was 4 or 5 was used as the starting compound in place of ethyl 5-bromo-2,2-dimethylpentanoate in REFERENCE EXAMPLE 8. The starting compound was reacted and treated in a manner similar to REFERENCE EXAMPLE 8 to prepare the compounds of REFERENCE EXAMPLES 9 and 10.

| Reference Example | Starting Compound | Product | Property |
|---|---|---|---|
| 9 | 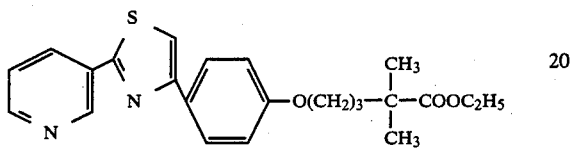 | | oily substance |
| 10 | | | oily substance |

EXAMPLE 1

Ethyl 5-[p-(2-bromoacetyl)phenoxy]-2,2-dimethyl-pentanoate, 1.8 g, obtained in REFERENCE EXAMPLE 1 and 0.7 g of 3-pyridylthioamide were stirred in 20 ml of methanol at room temperature for 5 hours. The solvent was removed from the reaction mixture by distillation and, 30 ml of chloroform and 30 ml of a 5% aqueous hydrogen sodium carbonate solution were added to the residue. After the mixture was stirred, the chloroform layer was fractionated and successively washed with water and an aqueous saturated sodium chloride solution followed by drying over anhydrous sodium sulfate. Chloroform was distilled off to give the oily residue.

The oily residue was subjected to silica gel column chromatography and the desired product was eluted out using chloroform-methanol (10:1 in a volume ratio) as an eluant. The solvent was removed from the eluate by distillation under reduced pressure to obtain the desired product, ethyl 2,2-dimethyl-5-[p-[2-(3-pyridyl)-4-thiazolyl]phenoxy]pentanoate as an oily substance.

NMR Spectrum (CDCl$_3$) (internal standard: TMS)
δ (ppm):

1.22(6H, s, CH$_3$—C—CH$_3$)

1.26(3H, t, J=7.2 Hz COOCH$_2$—CH$_3$)

1.5-1.9(4H, m, C—CH$_2$—CH$_2$—C)

3.99(2H, t, J=5.4 Hz, φ-O—CH$_2$—C)

4.12(2H, q, J=7.2 Hz, COOCH$_2$—C)

6.94(2H, d, J=8.3 Hz, 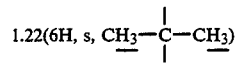)

-continued 7.38(1H, s 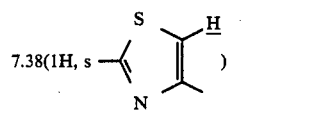)

7.38(1H, m, 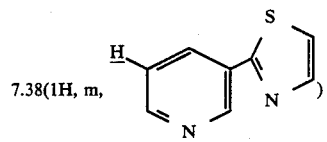)

8.30(1H, d, t, J=7.2 Hz, J=1.8 Hz, 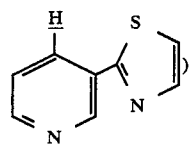)

8.64(1H, dd, J=4.3 Hz, J=1.8 Hz, 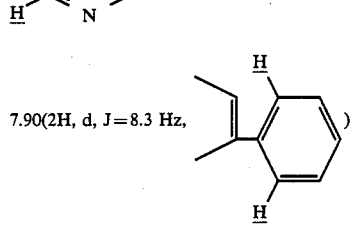)

7.90(2H, d, J=8.3 Hz, 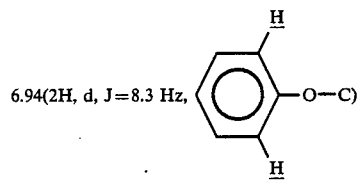)

8.20(1H, d, J=1.8 Hz, 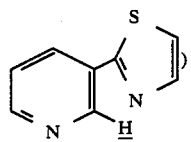)

EXAMPLE 2

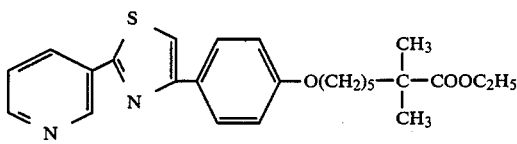

Ethyl 7-[p-(bromoacetyl)phenoxy]-2,2-dimethylheptanoate obtained in REFERENCE EXAMPLE 3 was used as the starting material in place of ethyl 5-[p-(2-bromoacetyl)phenoxy]-2,2-dimethylpentanoate in EXAMPLE 1. The starting material was reacted and treated in a manner similar to EXAMPLE 1. The resulting residue was recrystallized from petroleum ether to give the desired product, ethyl 2,2-dimethyl-7-[p-[2-(3-pyridyl)-4-thiazolyl]phenoxy]heptanoate, as white crystals.

Melting point: 41°–42° C.,

|  | Elemental Analysis (as $C_{25}H_{30}N_2O_3S$) | | | |
| --- | --- | --- | --- | --- |
|  | C (%) | H (%) | N (%) | S (%) |
| Calcd. | 68.46 | 6.89 | 6.39 | 7.31 |
| Found | 68.60 | 6.87 | 6.36 | 7.11 |

EXAMPLE 3

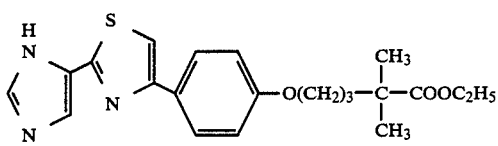

After 3.6 g of ethyl 5-[p-(bromoacetyl)phenoxy]-2,2-dimethylpentanoate obtained in REFERENCE EXAMPLE 1 and 1 g of 4-imidazolylthioamide were stirred in 40 ml of methanol at room temperature for 15 minutes, the mixture was stirred with heating under reflux at 70° C. for 2 hours. Then, the solvent was removed from the reaction mixture by distillation and, 200 ml of chloroform and 100 ml of a 5% aqueous hydrogen sodium carbonate solution were added to the residue. After stirring the mixture, the chloroform layer was fractionated and successively washed with water and then an aqueous saturated sodium chloride solution followed by drying over anhydrous sodium sulfate. Chloroform was removed by distillation to give an oily substance. The oily substance was subjected to silica gel column chromatography. The desired product was eluted out using chloroform-methanol (20:1 in a volume ratio) as an eluant. The solvent was removed from the eluate by distillation under reduced pressure. The residue was recrystallized from ethyl acetate to obtain the desired product, ethyl 5-[p-[2-(4-imidazolyl)-4-thiazolyl]phenoxy]-2,2-dimethylpentanoate as white crystals.

Melting point: 122°–123° C.,

|  | Elemental Analysis (as $C_{21}H_{25}N_3O_3S$) | | | |
| --- | --- | --- | --- | --- |
|  | C (%) | H (%) | N (%) | S (%) |
| Calcd. | 63.14 | 6.31 | 10.52 | 8.02 |
| Found | 63.21 | 6.25 | 10.46 | 8.14 |

EXAMPLE 4

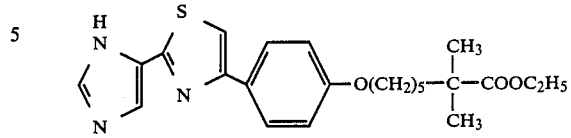

Ethyl 7-[p-(bromoacetyl)phenoxy]-2,2-dimethylheptanoate obtained in REFERENCE EXAMPLE 3 was used as the starting compound in place of ethyl 5-[p-(bromoacetyl)phenoxy]-2,2-dimethylpentanoate in EXAMPLE 3. The starting compound was reacted and treated in a manner similar to EXAMPLE 3 (except that recrystallization was performed from ethyl acetate-hexane) to obtain the desired product, ethyl 5-[p-[2-(4-imidazolyl)-4-thiazolyl]phenoxy]-2,2-dimethylheptanoate as white crystals.

Melting point: 114°–115° C.,

|  | Elemental Analysis (as $C_{23}H_{29}N_3O_3S$) | | | |
| --- | --- | --- | --- | --- |
|  | C (%) | H (%) | N (%) | S (%) |
| Calcd. | 64.61 | 6.84 | 9.83 | 7.50 |
| Found | 64.69 | 7.02 | 9.75 | 7.40 |

EXAMPLE 5

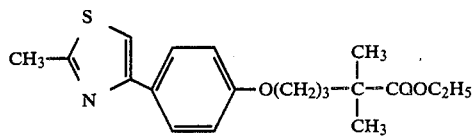

Thioacetamide was used as the starting compound in place of 4-imidazolylthioamide in EXAMPLE 3. The starting compound was reacted and treated in a manner similar to EXAMPLE 3. The resulting oily substance was subjected to silica gel column chromatography. The desired product was eluted out using chloroform as an eluant and the solvent was removed from the eluate by distillation under reduced pressure to obtain the desired product, ethyl 5-[p-(2-methyl-4-thiazolyl)-phenoxy]-2,2-dimethylpentanoate as an oily substance.

NMR Spectrum (CDCl$_3$) (internal standard: TMS)
δ(ppm):

1.20 (6H, s, CH$_3$—C—CH$_3$)

1.22 (3H, t, J=7.2Hz, COOC—CH$_3$)

1.5–1.9 (4H, m, C—CH$_2$—CH$_2$—C)

2.73 (3H, s, CH$_3$—⟨S/N⟩)

-continued 3.94 (2H, t, J=6.1Hz, φ-O—C$\underline{H_2}$—C)

4.08 (2H, q, J=7.2Hz, COO—C$\underline{H_2}$—C)

6.86 (2H, d, J=8.3Hz, 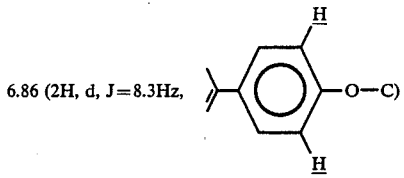 )

7.12 (1H, s, 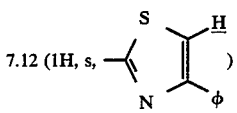 )

7.74 (2H, d, J=8.3Hz, 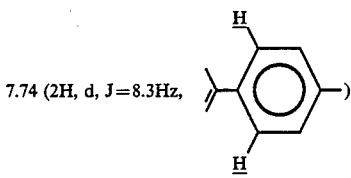 )

EXAMPLE 6

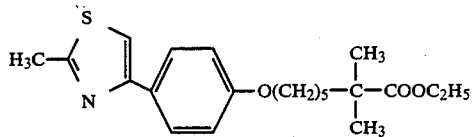

Thioacetamide was used as the starting compound in place of 3-pyridylacetamide in EXAMPLE 2. The starting compound was reacted and treated in a manner similar to EXAMPLE 1. The resulting oily substance was subjected to silica gel column chromatography. The desired product was eluted out using n-hexane-ethyl acetate (8:1 in a volume ratio) as an eluant and the solvent was removed from the eluate by distillation under reduced pressure to give the desired product, ethyl 7-[p-(2-methyl-4-thiazolyl)phenoxy]-2,2-dimethylheptanoate as an oily substance.

NMR Spectrum (CDCl$_3$) (internal standard: TMS) δ(ppm):

1.23 (3H, t, J=7.2Hz, C$\underline{H_3}$—CH$_2$—O—)

1.16 (6H, s, C$\underline{H_3}$—C—C$\underline{H_3}$)

1.1–1.9 (8H, m, 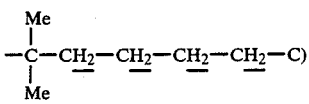 )

2.76 (3H, s,  )

3.98 (2H, t, J=6.1Hz, 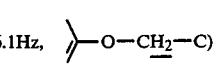 )

4.12 (2H, q, J=7.2Hz, COO—C$\underline{H_2}$—C)

6.92 (2H, d, J=9.0Hz, 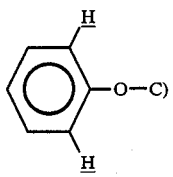 )

7.16 (1H, s, 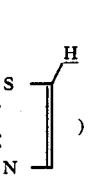 )

7.80 (1H, d, J=9.0Hz, 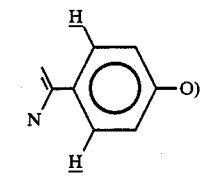 )

EXAMPLES 7 to 9

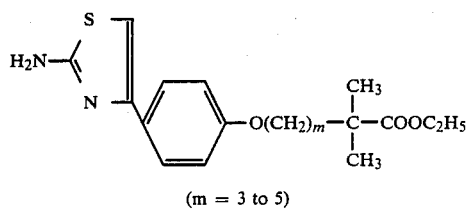

(m = 3 to 5)

The ethyl bromoacetylphenoxycarboxylates obtained in REFERENCE EXAMPLES 1 to 3 were used as the starting compounds in combination with thiourea. The starting compounds were reacted and treated in a manner similar to EXAMPLE 1 to prepare the compounds of EXAMPLES 7 to 9.

| EXAMPLE No. | Starting Compound REFERENCE EXAMPLE No. | Product Structural Formula | Melting Point (°C.) | Elemental Analysis C(%) H(%) N(%) S |
|---|---|---|---|---|
| 7 | 1 | $H_2N-\underset{N}{\overset{S}{\|}}\!\!=\!\!\bigcirc\!\!-O(CH_2)_3\underset{CH_3}{\overset{CH_3}{C}}-COOC_2H_5$<br>Ethyl 5-[p-(2-amino-4-thiazolyl)phenoxy]-2,2-dimethylpentanoate | 127–128 | (as $C_{18}H_{24}N_2O_3S$)<br>Calcd.<br>62.04  6.94  8.04  9<br>Found<br>61.88  7.05  7.86  9 |
| 8 | 2 | $H_2N-\underset{N}{\overset{S}{\|}}\!\!=\!\!\bigcirc\!\!-O(CH_2)_4\underset{CH_3}{\overset{CH_3}{C}}-COOC_2H_5$<br>Ethyl 6-[p-(2-amino-4-thiazolyl)-phenoxy]-2,2-dimethylhexanoate | 138–140 | (as $C_{19}H_{26}N_2O_3S$)<br>Calcd.<br>62.96  7.23  7.73  8.<br>Found<br>62.81  7.31  7.55  9. |
| 9 | 3 | $H_2N-\underset{N}{\overset{S}{\|}}\!\!=\!\!\bigcirc\!\!-O(CH_2)_5\underset{CH_3}{\overset{CH_3}{C}}-COOC_2H_5$<br>Ethyl 7-[p-(2-amino-4-thiazolyl)-phenoxy]-2,2-dimethylheptanoate | 117–119 | (as $C_{20}H_{28}N_2O_3S$)<br>Calcd.<br>63.80  7.50  7.44<br>Found<br>63.77  7.54  7.34 |

EXAMPLES 10 AND 11

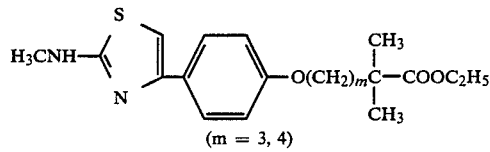

(m = 3, 4)

The ethyl bromoacetylphenoxycarboxylates obtained in REFERENCE EXAMPLES 1 and 2 were used as the starting compounds in combination with methyl thiourea. The starting compounds were reacted and treated in a manner similar to EXAMPLE 1 to prepare the compounds of EXAMPLES 10 and 11.

| EXAMPLE No. | Starting Compound REFERENCE EXAMPLE No. | Product Structural Formula | Melting Point (°C.) | Elemental Analysis C(%) H(%) N(%) S |
|---|---|---|---|---|
| 10 | 1 | $H_3CHN-\underset{N}{\overset{S}{\|}}\!\!=\!\!\bigcirc\!\!-O(CH_2)_3\underset{CH_3}{\overset{CH_3}{C}}-COOC_2H_5$<br>Ethyl 2,2-dimethyl-5-[p-2-methylamino-4-thiazolyl)phenoxy]-pentanoate | 65–66 | (as $C_{19}H_{26}N_2O_3S$)<br>Calcd.<br>62.96  7.23  7.73  8.<br>Found<br>62.96  7.46  7.63  8. |
| 11 | 2 | $H_3CHN-\underset{N}{\overset{S}{\|}}\!\!=\!\!\bigcirc\!\!-O(CH_2)_4\underset{CH_3}{\overset{CH_3}{C}}-COOC_2H_5$<br>Ethyl 2,2-dimethyl-6-[p-2-methylamino-4-thiazolyl)-phenoxy]hexanoate | 93–95 | (as $C_{20}H_{28}N_2O_3S$)<br>Calcd.<br>63.80  7.50  7.44  8.<br>Found<br>63.92  7.57  7.43  8. |

EXAMPLES 12 AND 13

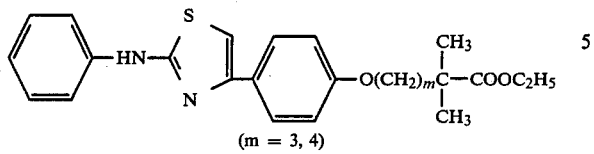

(m = 3, 4)

The ethyl bromoacetylphenoxycarboxylates obtained in REFERENCE EXAMPLES 1 and 2 were used as the starting compounds in combination with 1-phenyl-2-thiourea. The starting compounds were reacted and treated in a manner similar to EXAMPLE 1 to prepare the compounds of EXAMPLES 12 and 13.

EXAMPLES 14 TO 16

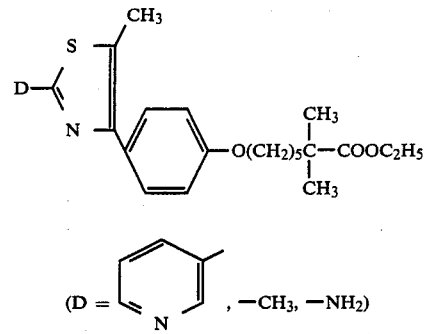

(D = 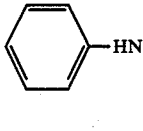, —CH$_3$, —NH$_2$)

Ethyl 7-[p-(2-bromopropionyl)phenoxy]-2,2-dimethylheptanoate obtained in REFERENCE EXAMPLE 5 was used in combination with 3-pyridylthioamide, thioacetamide and thiourea, respectively, as the starting compounds. The starting compounds were reacted and treated in a manner similar to EXAMPLE 3 to prepare the compounds of EXAMPLES 14 to 16.

| EXAMPLE No. | Starting Compound REFERENCE EXAMPLE No. | Product Structural Formula | Melting Point (°C.) | Elemental Analysis C(%) H(%) N(%) S(%) |
|---|---|---|---|---|
| 12 | 1 | 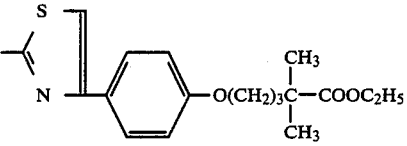 Ethyl 2,2-dimethyl-5-[p-2-phenylamino-4-thiazolyl)-phenoxy]pentanoate | 85–86 | (as $C_{24}H_{28}N_2O_3S$) Calcd. 67.90 6.65 6.60 7.7 Found 68.00 6.72 6.35 7.3 |
| 13 | 2 | 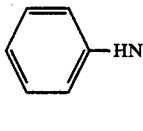 Ethyl 2,2-dimethyl-6-[p-2-phenylamino-4-thiazolyl)-phenoxy]hexanoate | 65–68 | (as $C_{25}H_{30}N_2O_3S$) Calcd. 68.46 6.89 6.39 7.3 Found 68.60 7.03 6.29 7.1 |

| EXAMPLE No. | Starting Compound | Product Structural Formula | Melting Point (°C.) | Elemental Analysis NMR Spectrum |
|---|---|---|---|---|
| 14 | 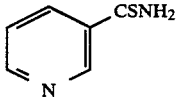 | 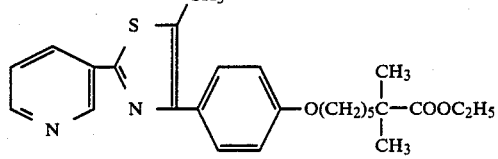 | oily substance | NMR Spectrum (CDCl$_3$) (internal standard: TMS) δ(ppm): 1.16(6H, s, C$\underline{H}_3$—C—C$\underline{H}_3$) 1.23(3H, t, J=7.2Hz, COO—C—C$\underline{H}_3$) 1.1–1.9(8H, m, C—C$\underline{H}_2$C$\underline{H}_2$—C$\underline{H}_2$C$\underline{H}_2$—C) |

-continued

| Ex-AMPLE No. | Starting Compound | Product Structural Formula | Melting Point (°C.) | Elemental Analysis NMR Spectrum |
|---|---|---|---|---|
| | | Ethyl 2,2-dimethyl-7-[p-[5-methyl-2-(3-pyridyl)-4-thaizolyl]phenoxy]heptanoate | | 2.62(3H, s, —⟨S/N⟩—Me) <br><br> 4.02(2H, t, 6.1Hz, >—O—CH₂—C) <br><br> 4.12(2H, q, J=7.2Hz, COOCH₂—C) <br> 6.98(2H, d, J=9Hz, phenyl-H) <br><br> NMR spectrum (CDCl₃) <br> (internal standard: TMS) <br> δ (ppm): <br> 7.34(1H, dd, J=8.3Hz, J=4.3Hz, pyridyl-H) <br><br> 7.66(2H, d, J=9Hz, phenyl-H) <br><br> 8.26(1H, d, t, J=8.3Hz, J=1.8Hz, pyridyl-H) <br><br> 8.64(1H, d, d, J=4.3Hz, J=1.8Hz, pyridyl-H) <br><br> 9.16(1H, d, J=1.8Hz, pyridyl-thiazolyl-H) |

-continued

| Example No. | Starting Compound | Product Structural Formula | Melting Point (°C.) | Elemental Analysis NMR Spectrum |
|---|---|---|---|---|
| 15 | CH₃CSNH₂ | (structure shown)<br><br>Ethyl 2,2-dimethyl-7-[p-2,5-dimethyl-4-thiazolyl)-phenoxy]heptanoate | oily substance | NMR spectrum (CDCl₃)<br>(internal standard: TMS)<br>δ(ppm):<br><br>1.16(6H, s, C$\underline{H}_3$—C—C$\underline{H}_3$)<br><br>1.23(3H, t, J=7.2Hz, C$\underline{H}_3$—CH₂—O—)<br>1.1~1.9(8H, m, —C—C$\underline{H}_2$—C$\underline{H}_2$—C$\underline{H}_2$—C$\underline{H}_2$—C)<br><br>2.46(3H, s, S—Me on thiazole)<br><br>2.64(3H, s, Me on thiazole)<br><br>3.98(2H, t, J=5.8Hz, phenyl—O—C$\underline{H}_2$—C)<br><br>4.12(2H, q, J=7.2Hz, COOC$\underline{H}_2$—C)<br>NMR Spectrum (CDCl₃)<br>(internal standard: TMS)<br>δ (ppm):<br>6.93(2H, d, J=9.0Hz, aromatic H)<br><br>7.54(2H, d, J=9.0Hz, aromatic H) |
| 16 | NH₂CSNH₂ | (structure shown)<br><br>Ethyl 7-[P-(2-amino-5-methyl-4-thiazolyl)phenoxy]-2,2-dimethyl | 93-94 | (as C₁₂H₃₀N₂O₃S)<br>C(%) H(%) N(%) S(%)<br>Calcd. 64.59 7.74 7.17 8.21<br>Found 64.58 7.85 7.05 8.10 |

EXAMPLE 17

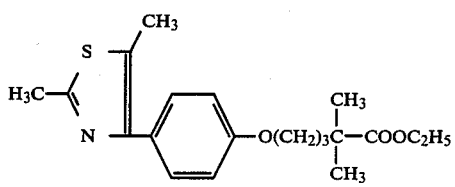

Ethyl 2,2-dimethyl-5-[p-(2-bromopropionyl)phenoxy]pentancate obtained in REFERENCE EXAMPLE 4 was used as the starting compound in place of ethyl 7-[p-(2-bromopropionyl)phenoxy]-2,2-dimethylheptanoate in EXAMPLE 15. The starting compound was reacted and treated in a manner similar to EXAMPLE 15. The resulting oily substance was subjected to silica gel column chromatography. The solvent was removed from the elute by distillation under reduced pressure to give the desired product, ethyl 5-[p-[2,5-dimethyl-4-thiazolyl)-4-thiazolyl]phenoxy]-2,2-dimethylpentanoate as an oily substance.

NMR Spectrum (CDCl$_3$) (internal standard: TMS) δ(ppm):

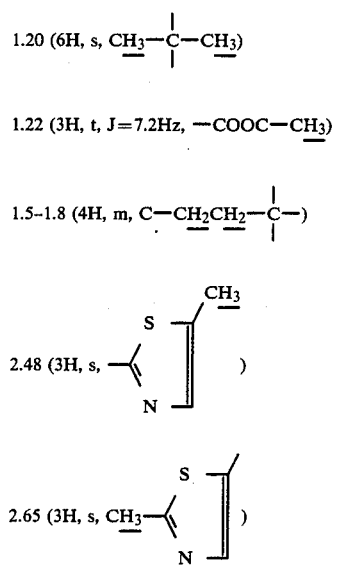

3.98 (2H, q, φ-OCH$_2$—C)

4.12 (2H, q, J=7.2Hz, COOCH$_2$C)

6.91 (2H, d, J=8.3Hz, 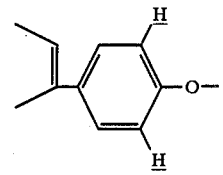

7.52 (2H, d, J=8.3Hz, 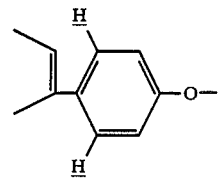

EXAMPLE 18

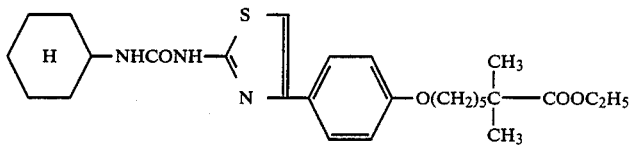

In 15 ml of tetrahydrofuran, 1.13 g of ethyl 7-[p-(2-amino-4-thiazolyl)phenoxy]-2,2-dimethylheptanoate obtained in EXAMPLE 9 was reacted with 0.38 g of cyclohexyl isocyanate overnight with heating under reflux.

Ice water was poured into the reaction mixture and then extracted with methylene chloride. After the methylene chloride layer was dried over anhydrous magnesium sulfate, the solvent was removed under reduced pressure. The resulting residue was subjected to silica gel column chromatography. The product was eluted out using n-hexane-ethyl acetate (4:1 in a volume ratio) as an eluant. After the solvent was removed in vaccuo, the resulting crystals were recrystallized from a solvent mixture of n-hexane-ether to give ethyl 7-[p-[2-(3-cyclohexylureido)-4-thiazolyl]phenoxy]-2,2-dimethylheptanoate as white crystals.

Melting point: 106°–108° C.

| Elemental Analysis (as C$_{27}$H$_{39}$N$_3$O$_4$S) | | | | |
|---|---|---|---|---|
| | C (%) | H (%) | N (%) | S (%) |
| Calcd. | 64.64 | 7.84 | 8.38 | 6.39 |
| Found | 64.43 | 8.04 | 8.24 | 6.40 |

EXAMPLE 19

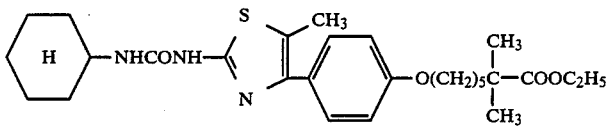

Ethyl 7-[p-(2-amino-5-methyl-4-thiazolyl)phenoxy]-2,2-dimethylheptanoate obtained in EXAMPLE 16 was used as a starting compound in place of ethyl 7-[p-(2-amino-4-thiazolyl)phenoxy]-2,2-dimethylheptanoate in EXAMPLE 18. The starting compound was reacted and treated in a manner similar to EXAMPLE 18 to give the desired product, ethyl 7-[p-[2-(3-cyclohexylureido)-5-methyl-4-thiazolyl]phenoxy]-2,2-dimethylheptanoate as white crystals.

Melting point: 79°–81° C.

| Elemental Analysis (as $C_{27}H_{36}N_4O_4S$) | | | |
|---|---|---|---|
| C (%) | H (%) | N (%) | S (%) |
| Calcd. 63.26 | 7.08 | 10.93 | 6.25 |
| Found 63.01 | 7.08 | 10.85 | 6.13 |

EXAMPLE 21

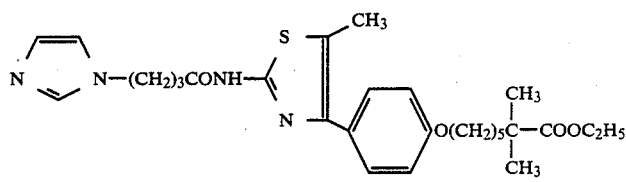

Ethyl 7-[p-(2-amino-5-methyl-4-thiazolyl)phenoxy]-2,2-dimethylheptanoate obtained in EXAMPLE 16 was used as a starting compound in place of ethyl 7-[p-(2-amino-4-thiazolyl)phenoxy]-2,2-dimethylheptanoate in EXAMPLE 20. The starting material was reacted and treated in a manner similar to EXAMPLE 20 to give the desired product, ethyl 7-[p-[2-[4-(1-imidazolyl)butyramido]-5-methyl-4-thiazolyl]phenoxy]-2,2-dimethylheptanoate as white crystals.

Melting point: 85°–87° C.

| Elemental Analysis (as $C_{28}H_{38}N_4O_4S$) | | | |
|---|---|---|---|
| C (%) | H (%) | N (%) | S (%) |
| Calcd. 63.85 | 7.27 | 10.64 | 6.09 |
| Found 63.87 | 7.47 | 10.62 | 6.25 |

EXAMPLE 22

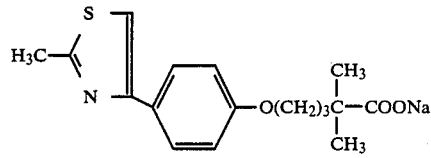

In 5 ml of ethanol was dissolved 1.40 g of ethyl 2,2-dimethyl-5-[p-(2-methyl-4-thiazolyl)phenoxy]pentanoate obtained in EXAMPLE 5. The solution was added to an aqueous sodium hydroxide solution (0.4 g of so-

| Elemental Analysis (as $C_{28}H_{41}N_3O_4S$) | | | |
|---|---|---|---|
| C (%) | H (%) | N (%) | S (%) |
| Calcd. 65.21 | 8.01 | 8.15 | 6.22 |
| Found 65.33 | 8.22 | 8.03 | 6.20 |

EXAMPLE 20

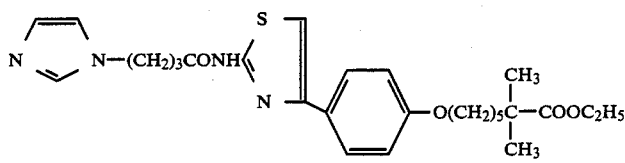

In 15 ml of dry N,N-dimethylformamide (DMF) were dissolved 0.39 g of 4-(1-imidazolyl)butyric acid and 0.37 g of 1-hydroxybenzotriazole. While stirring, 0.57 g of dicyclohexylcarbodiimide was added to the solution at 40° to 45° C. After dicyclohexylurea was precipitated out in the reaction mixture, a solution of 0.94 g of ethyl 7-[p-(2-amino-4-thiazolyl)phenoxy]-2,2-dimethylheptanoate in 5 ml of DMF was dropwise added to the mixture at the same temperature and the mixture was stirred at the same temperature overnight. After removing dicyclohexylurea by filtration, the filtrate was condensed under reduced pressure. Ice water was added to the residue followed by extracting with chloroform. After the chloroform layer was washed successively with a saturated aqueous hydrogen sodium carbonate and water, the chloroform layer was dried over anhydrous sodium magnesium. The chloroform was removed by distillation under reduced pressure and the resulting residue was subjected to silica gel column chromatography. The product was eluted out using chloroform-methanol (40:1 in a volume ratio) as an eluant. After the solvent was removed by distillation, the resulting crystals were recrystallized from a solvent mixture of ether-benzene to give ethyl 7-[p-[2-[4-(1- dium hydroxide in 5 ml of water) and the mixture refluxed for 10 hours. After cooling, the precipitated crystals was washed with water to obtain the desired product, sodium 2,2-dimethyl-5-[p-(2-methyl-4-thiazolyl)phenoxy]pentanoate as white crystals.

Melting point: 259°–261° C.

| Elemental Analysis (as $C_{17}H_{20}NO_3SNa$) | | | | |
| --- | --- | --- | --- | --- |
| | C (%) | H (%) | N (%) | S (%) |
| Calcd. | 59.81 | 5.90 | 4.10 | 9.39 |
| Found | 58.72 | 5.73 | 4.12 | 9.34 |

EXAMPLE 23

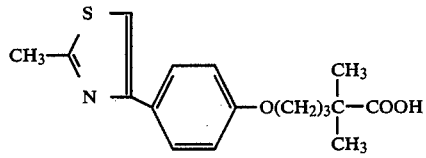

In 50 ml of water was dissolved 1.0 g of sodium 2,2-dimethyl-5-[p-(2-methyl-4-thiazolyl)phenoxy]pentanoate obtained in EXAMPLE 22. The solution was neutralized with 10% hydrochloric acid. The precipitated crystals were taken out by filtration and washed with water to give the desired product, 2,2-dimethyl-5-[p-(2-methyl-4-thiazolyl)phenoxy]pentanoic acid as white crystals.

Melting point: 150°–153° C.

| Elemental Analysis (as $C_{17}H_{21}NO_3S$) | | | | |
| --- | --- | --- | --- | --- |
| | C (%) | H (%) | N (%) | S (%) |
| Calcd. | 63.92 | 6.63 | 4.39 | 10.04 |
| Found | 63.67 | 6.65 | 4.13 | 9.64 |

EXAMPLE 24

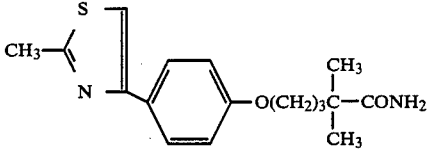

In 10 ml of dichloromethane were dissolved 0.7 g of 2,2-dimethyl-5-[p-(2-methyl-4-thiazolyl)phenoxy]pentanoic acid obtained in EXAMPLE 23 and 0.22 g of triethyl amine. The solution was cooled to −20° to −15° C. while stirring and 0.3 g of isobutyl chloroformate was dropwise added thereto. After stirring for 30 minutes at the same temperature, 0.6 g of conc. ammonia water (ammonia 29%) was dropwise added to the mixture. After completion of the dropwise addition, the temperature was elevated to room temperature and stirring was continued for a further 15 minutes.

Ice water was poured into the reaction solution and the organic layer was fractionated. The organic layer was successively washed with a saturated aqueous hydrogen sodium carbonate solution and water and then dried over anhydrous magnesium sulfate. After the solvent was removed under reduced pressure and the resulting residue was subjected to silica gel column chromatography. The product was eluted out using chloroform-methanol (50:1 in a volume ratio) as an eluant. After the solvent was removed in vacuo, the formed crystals were recrystallized from a solvent mixture of ether-benzene to give the desired product, 2,2-dimethyl-5-[p-(2-methyl-4-thiazolyl)phenoxy]pentamide, as white crystals.

Melting point: 148°–150° C.

| Elemental Analysis (as $C_{17}H_{22}N_2O_2S$) | | | | |
| --- | --- | --- | --- | --- |
| | C (%) | H (%) | N (%) | S (%) |
| Calcd. | 64.12 | 6.96 | 8.80 | 10.07 |
| Found | 64.20 | 7.04 | 8.78 | 9.95 |

EXAMPLE 25

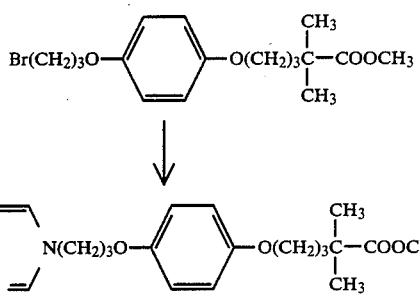

After 210 mg of sodium hydride (60% suspension in mineral oil) was washed with dry benzene, 20 ml of dry N,N-dimethylformamide was added thereto and 360 mg of imidazole was further added with stirring. After vigorous bubbling was retarded, the suspension was heated at 80° C. for 30 minutes with stirring and then cooled to room temperature. A solution of 1.8 g of methyl 5-[p-(3-bromopropoxy)phenoxy]-2,2-dimethylpentanoate in 5 ml of dry N,N-dimethylformamide was added to the suspension and stirring was continued at 60° C. for 4 hours. Thereafter the solvent was removed from the reaction mixture by distillation under reduced pressure. The residual oily substance was dissolved in methylene chloride. The solution was successively washed with a 5% aqueous hydrogen sodium carbonate, water and a saturated aqueous sodium chloride solution and then dried over anhydrous sodium sulfate. After drying, the solvent was removed by distillation under reduced pressure, the remained oily substance was subjected to silica gel column chromatography. The product was eluted out using a chloroform-methanol liquid mixture (50:1) as an eluant. The solvent was removed from the eluate by distillation under reduced pressure and the residue was recrystallized from a mixture of ethyl acetate-n-hexane to give the desired product, methyl 5-[p-[3-(1-imidazolyl)propoxy]phenoxy]-2,2-dimethylpentanoate.

Melting point: 47°–49° C.

| Elemental Analysis (as $C_{20}H_{28}N_2O_4$) | | | |
| --- | --- | --- | --- |
| | C (%) | H (%) | N (%) |
| Calcd. | 66.64 | 7.83 | 7.77 |
| Found | 66.75 | 7.94 | 7.73 |

EXAMPLE 26

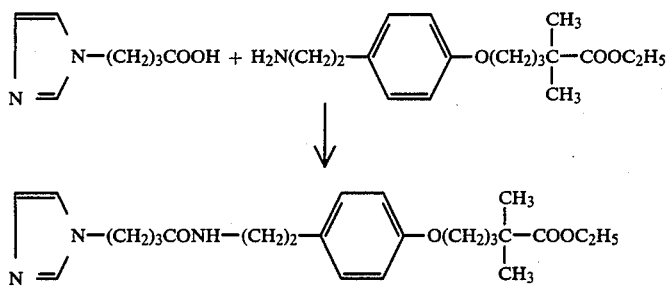

A solution of 1.6 g of 4-(1-imidazolyl)butyric acid and 1.4 g of 1-hydroxybenzotriazole in 100 ml of N,N-dimethylformamide was heated at 40° to 50° C. and 2.1 g of N,N'-dicyclohexylcarbodiimide was added to the solution under stirring. After stirring was continued for about 30 minutes, a solution of 3.0 g of ethyl 5-[p-(2-aminoethyl)phenoxy]-2,2-dimethylpentanoate in 15 ml of dry N,N-dimethylformamide was slowly dropwise added to the mixture. Stirring was continued at the same temperature for about 1 hour.

The precipitated dicyclohexyl urea was removed by filtration and the filtrate was condensed by distillation under reduced pressure. The remaining oily substance was dissolved in chloroform. The solution was successively washed with a 5% aqueous hydrogen sodium carbonate solution, water and a saturated aqueous sodium chloride solution and then dried over anhydrous sodium sulfate. The solvent was removed by distillation under reduced pressure and the remaining oily substance was subjected to silica gel column chromatography. The product was eluted out using chloroform-methanol (9:1) as an eluant. The solvent was removed from the eluate by distillation under reduced pressure to give the desired product, ethyl 5-[p-[2-[4-(1-imidazolyl)-butylamido]ethyl]phenoxy]-2,2-dimethylpentanoate as an oily substance.

NMR Spectrum (CDCl$_3$) (internal standard: TMS)
δ (ppm):

1.25 (T, 3H, C$\underline{H_3}$—, J = 7.2Hz)

1.20 (s, 6H, CH$_3$—C̲—CH$_3$)

1.6–1.8 (m, 4H, N—C—C$\underline{H_2}$—C, —O—C—C$\underline{H_2}$—C)

2.0–2.2 (m, 4H, C—C$\underline{H_2}$—C—N,
         ‖
         O

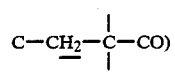

-continued

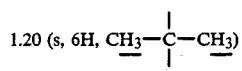, J = 7.2Hz)

3.49 (q, 2H, CONH—C$\underline{H_2}$—C, J = 7.2Hz)

3.8–4.1 (m, 4H, 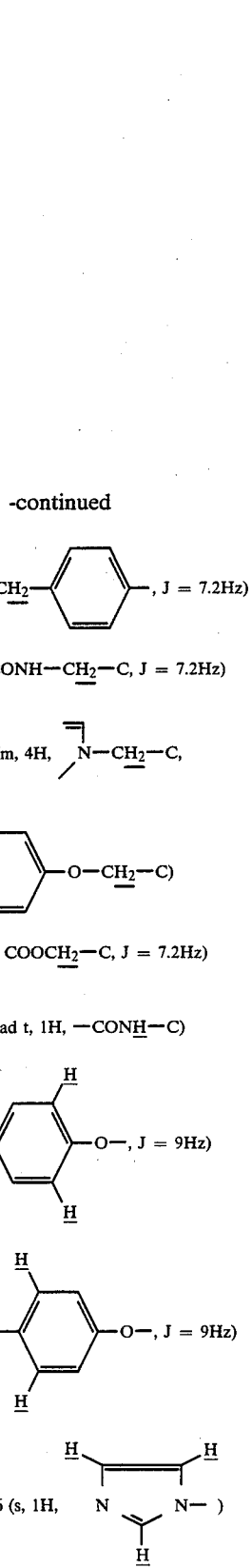

EXAMPLE 27

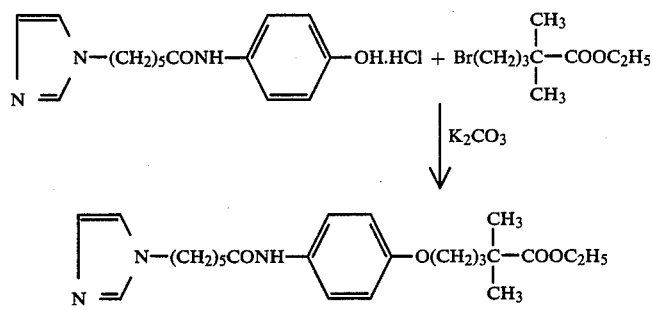

In 50 ml of ethanol was suspended 3 g of 4'-hydroxy-6-(1-imidazolyl)hexaneanilide hydrochloride. While stirring 2.8 g of anhydrous potassium carbonate and 2.4 g of ethyl 5-bromo-2,2-dimethylpentanoate were added to the suspension. The mixture was stirred for 8 hours under reflux. The solvent was removed from the reaction mixture by distillation under reduced pressure and the residue was dissolved in ethylene chloride. The solution was successively washed with a 5% aqueous hydrogen sodium carbonate solution, water and a saturated aqueous sodium chloride solution and then dried over anhydrous sodium sulfate. After drying, the solvent was removed by distillation under reduced pressure. The resulting crystals were recrystallized from ethyl acetate to give the aimed product, ethyl 5-[p-[6-(1-imidazolyl)hexanamido]phenoxy]-2,2-dimethylpentanoate.

Melting point: 81°–82° C.

| Elemental Analysis (as $C_{24}H_{35}N_3O_4$) | | | |
|---|---|---|---|
| | C (%) | H (%) | N (%) |
| Calcd. | 67.11 | 8.21 | 9.78 |
| Found | 66.93 | 8.44 | 9.79 |

EXAMPLE 28

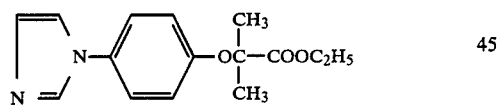

In 50 ml of ethanol was dissolved 1.6 g of p-(1-imidazolyl)phenol and 1.4 g of anhydrous potassium carbonate was added to the solution. While stirring, 2.1 g of ethyl α-bromoisobutyrate was dropwise added to the mixture. Thereafter stirring was continued for 20 hours under reflux. After cooling to room temperature, the solvent was removed from the reaction mixture in vaccuo. The residue was dissolved in methylene chloride. After the solution was successively washed with a 5% aqueous hydrogen sodium carbonate solution, water and a saturated aqueous sodium chloride solution, the solution was dried over anhydrous sodium sulfate. After drying, the solvent was removed by distillation under reduced pressure and the residue was subjected to silica gel column chromatography. The product was eluted out using chloroform-methanol (9:1) as an eluant. The solvent was removed from the eluate under reduced pressure to give the desired product, ethyl 2-[p-(1-imidazolyl)phenoxy]-2-methylpropionate, as an oily substance.

NMR Spectrum ($CDCl_3$) (internal standard: TMS) (ppm):

1.26 (t, 3H, —$\underline{CH_3}$, J = 5.5Hz)

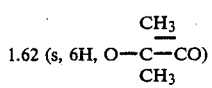

4.26 (q, 2H, COO$\underline{CH_2}$—C, J = 5.5Hz)

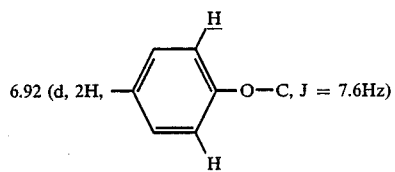

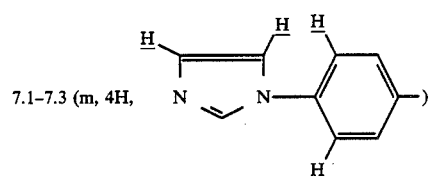

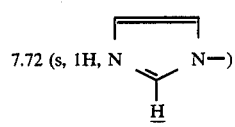

EXAMPLE 29

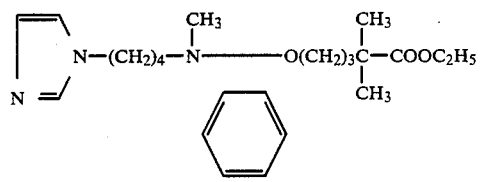

p-[N-[4-(1-Imidazolyl)butyl]-N-methylamino]phenol was used in place of 4'-hydroxy-6-(1-imidazolyl)hexananilide hydrochloride and reacted and treated in a manner similar to EXAMPLE 27 to give the desired product, ethyl 5-[p-[N-[4-(1-imidazolyl)]butyl-N-methylamino]phenoxy]-2,2-dimethylpentanoate, as an oily substance.

NMR Spectrum ($CDCl_3$) (internal standard: TMS)

-continued
δ (ppm):

1.22 (s, 6H, CH$_3$—C—CH$_3$) 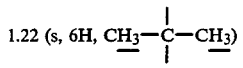

1.24 (t, 3H, —C—CH$_3$, J = 6.5Hz)

1.5–1.9 (m, 4H, N—C—CH$_2$CH$_2$—C—)

1.9–2.1 (m, 2H, C—CH$_2$—C—) 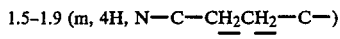

3.24 (s, 3H, N—CH$_3$)

3.6–4.2 (m, 4H, 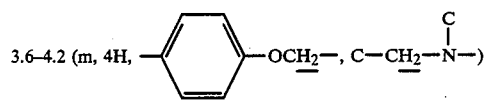 —OCH$_2$—, C—CH$_2$—N—)

4.44 (broad t, 2H, N⏜N—CH$_2$—C)

4.12 (q, 2H, COOCH$_2$—, J = 6.5Hz)

6.92 (d, 2H, 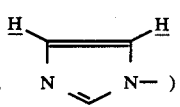, J = 9Hz)

7.40, 7.52 (broad s, 2H, N⏜N—)

7.74 (d, 2H, —N— 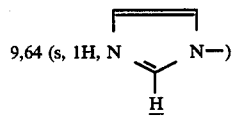)

9.64 (s, 1H, N⏜N—)

EXAMPLE 30

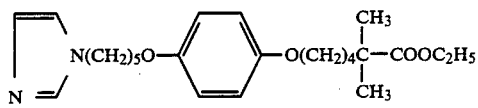

After 300 ml of ethanol was added to 35 g of p-[5-(1-imidazolyl)pentyloxy]phenol and 39 g of potassium carbonate, the mixture was heated at 60° C. with stirring and then cooled to room temperature. A solution of 43 g of ethyl 6-bromo-2,2-dimethylhexanoate in 50 ml of ethanol was added to the reaction mixture, and then the mixture was stirred under reflux overnight. The solvent was removed from the reaction mixture by distillation under reduced pressure and the residue was dissolved in chloroform. The solution was successively washed with a 1N aqueous sodium hydroxide solution, water, a saturated aqueous sodium chloride solution and then dried over anhydrous sodium sulfate. After drying, the solvent was removed by distillation under reduced pressure and the residue was subjected to silica gel column chromatography. The product was eluted out using a chloroform-methanol liquid mixture (30:1) as an eluant. The solvent was removed from the eluate by distillation. The residue was recrystallized from a mixture of ethyl acetate-n-hexane to give the desired product, ethyl 6-[p-[5-(1-imidazolyl)pentyloxy]phenoxy]-2,2-dimethylhexanoate.

Melting point: 40°–41° C.

| Elemental Analysis (as C$_{24}$H$_{36}$N$_2$O$_4$) | | | |
|---|---|---|---|
| | C (%) | H (%) | N (%) |
| Calcd. | 69.20 | 8.71 | 6.72 |
| Found | 69.11 | 8.94 | 6.67 |

EXAMPLE 31

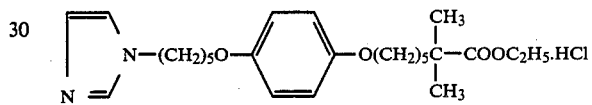

Ethyl 7-bromo-2,2-dimethylheptanoate was used as a starting compound in place of ethyl 6-bromo-2,2-dimethylhexanoate in EXAMPLE 30. The starting compound was reacted and treated in a manner similar to EXAMPLE 30. To the resulting oily substance was added methanol saturated with hydrogen chloride. The solvent was removed by distillation under reduced pressure. The residue was recrystallized from ethyl acetate to give the desired product, ethyl 7-[p-[5-(1-imidazolyl)pentyloxy]phenoxy]-2,2-dimethylheptanoate hydrochloride.

Melting point: 123°–124° C.

| Elemental Analysis (as C$_{25}$H$_{39}$N$_2$ClO$_4$) | | | | |
|---|---|---|---|---|
| | C (%) | H (%) | N (%) | Cl(%) |
| Calcd. | 64.29 | 8.42 | 6.00 | 7.59 |
| Found | 63.99 | 8.48 | 5.88 | 7.59 |

EXAMPLE 32

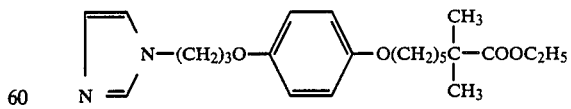

p-[3-(1-Imidazolyl)propoxy]phenol and ethyl 7-bromo-2,2-dimethylheptanoate were used as starting compounds in place of p-[5-(1-imidazolyl)pentyloxy]phenol and ethyl 6-bromo-2,2-dimethylhexanoate, respectively, in EXAMPLE 30. The starting compounds were heated and treated in a manner similar to EXAMPLE 30 to give the desired product, ethyl 7-[p-[3-(1- imidazolyl)propoxy]phenoxy]-2,2-dimethylheptanoate, as an oily substance.

NMR Spectrum (CD$_3$OD + DMSO-d$_6$ + DCl) (internal standard: TMS) δ (ppm):

1.16 (6H, s, 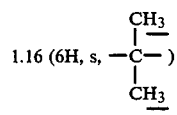)

1.24 (3H, t, J = 7.2Hz, —COO—CH$_2$—C$\underline{H_3}$)

1.2–1.9 (8H, m, 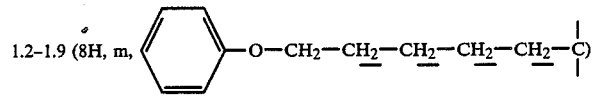)

2.37 (2H, quin, J = 5.8Hz, 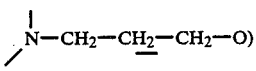)

3.90 (2H, t, J = 5.8Hz, 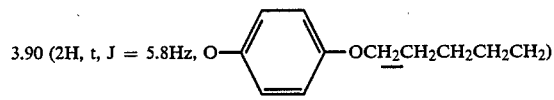)

4.0 (2H, t, J = 5.8Hz, 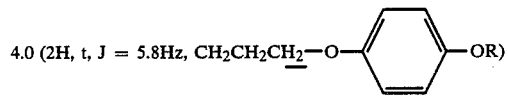)

4.10 (2H, q, J = 7.2Hz, —COOC$\underline{H_2}$—CH$_3$)

4.32 (2H, t, J = 5.8Hz, 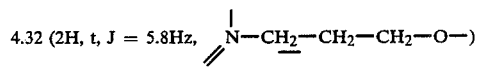)

6.82 (4H, s, 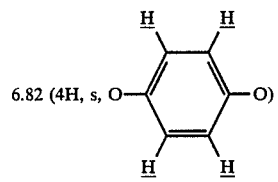)

7.56 (2H, s 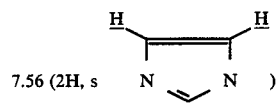)

9.16 (1H, t, J = 1.8Hz, 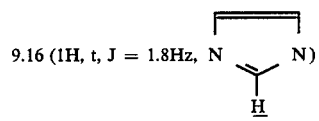)

EXAMPLE 33

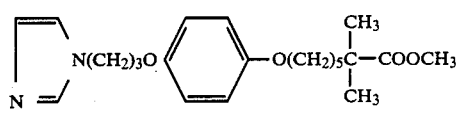

After 110 mg of sodium hydride (60% suspension in mineral oil) was washed with dry benzene, 10 ml of dry dimethylformamide was added thereto and 190 mg of imidazole was further added with stirring. After vigorous bubbling was retarded, the suspension was heated at 80° C. for 30 minutes with stirring and then cooled to room temperature. A solution of 870 mg of methyl 7-[p-(3-bromopropoxy)phenyloxy]-2,2-dimethylheptanoate in 10 ml of dry dimethylformamide was added to the suspension and stirring was continued at 60° C. for 5 hours. Thereafter the solvent was removed from the reaction mixture by distillation under reduced pressure. The residual oily substance was dissolved in benzene. The benzene layer was successively washed with an aqueous saturated hydrogen sodium carbonate solution, water and a saturated aqueous sodium chloride solution and then dried over anhydrous sodium sulfate.

After drying, the solvent was removed by distillation under reduced pressure, the remained oily substance was subjected to silica gel column chromatography. The product was eluted out using a chloroform-methanol mixture (50:1) as an eluant. The solvent was removed from the eluate by distillation under reduced pressure to give the desired product, methyl 7-[p-[3-(1-imidazolyl)propoxy]phenoxy]-2,2-dimethylheptanoate, as an oily substance.

NMR Spectrum (CDCl₃) (internal standard: TMS)

δ (ppm):

1.16 (6H, s, 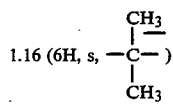)

1.2–1.9 (8H, m, 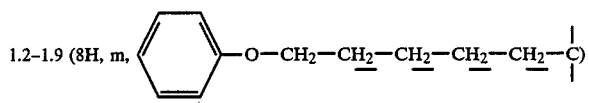)

2.18 (2H, quin, J = 5.8Hz, 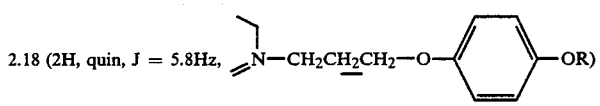)

3.64 (3H, s, COO<u>CH₃</u>)

3.8–4.0 (4H, m, 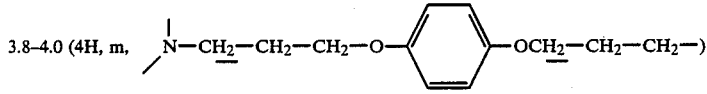)

4.18 (2H, t, J = 5.8Hz, 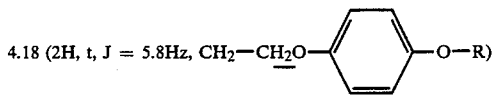)

6.78 (4H, s, 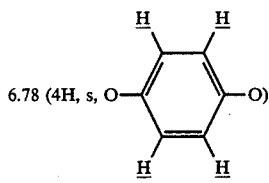)

6.88 (1H, s 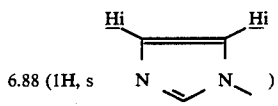)

7.04 (1H, s 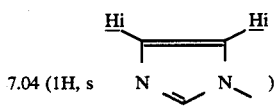)

7.48 (1H, s 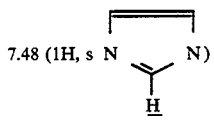)

EXAMPLE 34

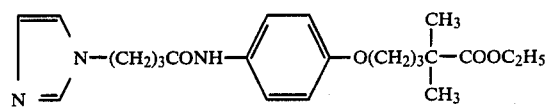

In 20 ml of dimethylformamide were dissolved 0.62 g of 4-(1-imidazolyl)butyric acid and 0.59 g of 1-hydroxybenzotriazole. While stirring, 0.91 g of dicyclohexylcarbodiimide was added to the solution at 40°–45° C. After dicyclohexylurea was precipitated in the reaction solution, a solution of ethyl 5-(p-amino)phenoxy-2,2- dimethylpentanoate in 5 ml of dimethylformamide was dropwise added thereto at the same temperature. The mixture was stirred at the same temperature for 1 hour. After dicyclohexylurea was removed by filtration, the filtrate was condensed under reduced pressure. Ice water was poured into the residue followed by extracting with chloroform. After the chloroform layer was successively washed with a saturated aqueous hydrogen sodium carbonate solution, water and a saturated aqueous sodium chloride solution, the chloroform layer was dried over anhydrous magnesium sulfate. After chloroform was removed by distillation under reduced pressure, the resulting residue was subjected to silica gel column chromatography. The product was eluted out using a chloroform-methanol liquid mixture (40:1 in a volume ratio) as an eluant. After the solvent was removed from the eluate by distillation under reduced pressure, the remained white solid was recrystallized from a solvent mixture of ether-benzene to give ethyl 5-[p-[4-(1-imidazolylbutylamido]phenoxy]-2,2-dimethylpentanoate, as white crystals.

Melting point: 92°–93° C.

| Elemental Analysis (as $C_{22}H_{31}N_3O_4$) | | | |
|---|---|---|---|
| | C (%) | H (%) | N (%) |
| Calcd. | 65.81 | 7.78 | 10.47 |
| Found | 65.80 | 7.68 | 10.38 |

EXAMPLES 35 TO 39

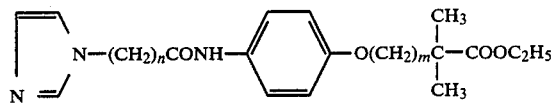

In addition to the starting compound used in EXAMPLE 34, 5-(1-imidazolyl)pentanoic acid (n=4) or ethyl p-aminophenoxycarboxylates (m=3, 4 and 5) were used as starting compounds by varying the combination thereof.

| Example No. | $\underset{N}{\boxed{\phantom{N}}}N-(CH_2)_n COOH$ | Product | Melting Point (°C.) | Elementary Analysis | | | |
|---|---|---|---|---|---|---|---|
| 35 | $\underset{N}{\boxed{\phantom{N}}}N-(CH_2)_3COOH$<br>4-(1-Imidazolyl)butyric acid | $\underset{N}{\boxed{\phantom{N}}}N-(CH_2)_3CONH-\bigcirc-O(CH_2)_4-C(CH_3)_2-COOC_2H_5$<br>Ethyl 6-[P-[4-(1-imidazolyl)-butylamido]phenoxy]-2,2-dimethyl hexanoate | 109–110 | as $C_{23}H_{33}N_3O_4$:<br>Calcd.<br>Found | C(%)<br>66.48<br>66.64 | H(%)<br>8.00<br>8.21 | N(%)<br>10.11<br>10.12 |
| 36 | " | $\underset{N}{\boxed{\phantom{N}}}N-(CH_2)_3CONH-\bigcirc-O(CH_2)_5-C(CH_3)_2-COOC_2H_5$<br>Ethyl-7-[P-[4-(1-imidazolyl)butyramide]-phenoxy]-2,2-dimethyl heptanoate | 80–82 | as $C_{24}H_{35}N_3O_4$:<br>Calcd.<br>Found | C(%)<br>67.11<br>67.14 | H(%)<br>8.21<br>8.17 | N(%)<br>9.78<br>9.75 |
| 37 | $\underset{N}{\boxed{\phantom{N}}}N-(CH_2)_4COOH$<br>5-(1-imidazolyl)pentanoic acid | $\underset{N}{\boxed{\phantom{N}}}N-(CH_2)_4CONH-\bigcirc-O(CH_2)_3-C(CH_3)_2-COOC_2H_5$<br>Ethyl 5-[P-[5-imidazolyl)-valeramido]phenoxy]-2,2-dimethylpentanoate | 77–78 | as $C_{23}H_{33}N_3O_4$:<br>Calcd.<br>Found | C(%)<br>66.48<br>66.30 | H(%)<br>8.00<br>7.94 | N(%)<br>10.11<br>10.11 |

-continued

| Example No. | $N\overset{\frown}{\smile}N-(CH_2)_n COOH$ | Product | Melting Point (°C.) | Elementary Analysis | | |
|---|---|---|---|---|---|---|

| 38 | " | $N\overset{\frown}{\smile}N-(CH_2)_4 CONH-\underset{-O(CH_2)_4-\underset{CH_3}{\overset{CH_3}{\underset{|}{C}}}-COOC_2H_5}{\bigcirc}$ Ethyl-6-[P-[5-(1-imidazolyl)-pentanamide]phenoxy]-2,2-dimethyl hexanoate | 71–72 | as $C_{24}H_{35}N_3O_4$: Calcd. Found | C(%) 67.11 67.31 | H(%) 8.21 8.32 | N(%) 9.78 9.56 |
| 39 | $N\overset{\frown}{\smile}N-(CH_2)_4 COOH$ | $N\overset{\frown}{\smile}N-(CH_2)_4 CONH-\underset{-O(CH_2)_5-\underset{CH_3}{\overset{CH_3}{\underset{|}{C}}}-COOC_2H_5}{\bigcirc}$ Ethyl-7-[P-[5-(1-imidazolyl)-valeramido]phenoxy]-2,2-dimethyl-heptanoate | 89–91 | as $C_{25}H_{37}N_3O_4$: Calcd. Found | C(%) 67.69 67.43 | H(%) 8.41 8.37 | N(%) 9.47 9.40 |

EXAMPLE 40

$N\overset{\frown}{\smile}N-(CH_2)_5 CONH-\bigcirc-O(CH_2)_4\underset{CH_3}{\overset{CH_3}{\underset{|}{C}}}-COOC_2H_5$ To 20 ml of ethanol were added 1.37 g of p-hydroxy-6-(1-imidazolyl)hexaneanilide and 0.69 g of anhydrous potassium carbonate and the mixture was stirred for 30 minutes with heating under reflux. After cooling, 1.26 g of ethyl 6-bromo-2,2-dimethylhexanoate was added thereto and the mixture was reacted overnight with heating under reflux. The solvent was removed from the reaction mixture by distillation under reduced pressure. Water was added to the resulting residue followed by extracting with chloroform. After the chloroform layer was successively washed with a 1N aqueous sodium hydroxide solution and a saturated aqueous sodium chloride solution, it was dried over anhydrous magnesium sulfate. The solvent was removed by distillation under reduced pressure and the resulting residue was subjected to silica gel column chromatography. The product was eluted out using a chloroform-methanol liquid mixture (50:1 in a volume ratio). The solvent was removed by distillation under reduced pressure. The resulting crystals were recrystallized from a solvent mixture of n-hexane-ethylacetate to obtain ethyl 6-[p-[6-(1-imidazolyl)hexanamido]phenoxy]-2,2-dimethylhexanoate as white crystals.

Melting point: 64°–65° C.

| Elemental Analysis (as $C_{25}H_{37}N_3O_4$) | | | |
|---|---|---|---|
| | C (%) | H (%) | N (%) |
| Calcd. | 67.69 | 8.41 | 9.47 |
| Found | 67.48 | 8.65 | 9.46 |

EXAMPLE 41

$N\overset{\frown}{\smile}N-(CH_2)_5 CONH-\bigcirc-O(CH_2)_5\underset{CH_3}{\overset{CH_3}{\underset{|}{C}}}-COOC_2H_5$ Ethyl 7-bromo-2,2-dimethylheptanoate was used as a starting compound in place of ethyl 6-bromo-2,2-dimethylhexanoate in EXAMPLE 40. The starting compound was reacted and treated in a manner similar to EXAMPLE 40 to give ethyl 7-[p-[6-(1-imidazolyl)hexanamido]-phenoxy]-2,2-dimethylheptanoate.

Melting point: 59°–59° C.

| Elemental Analysis (as $C_{26}H_{39}N_3O_4$) | | | |
|---|---|---|---|
| | C (%) | H (%) | N (%) |
| Calcd. | 68.24 | 8.59 | 9.18 |
| Found | 68.28 | 8.72 | 9.10 |

EXAMPLE 42

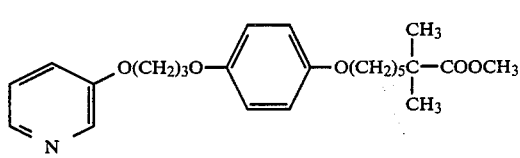

3-Hydroxypyridine was used as a starting compound in place of imidazole in EXAMPLE 33. The starting compound was reated and treated in a manner similar to EXAMPLE 33 to give the desired product, methyl 7-[p-[3-(3-pyridyloxy)propoxy]phenoxy]-2,2-dimethyl-heptanoate, as an oily substance.

NMR Spectrum (CDCl$_3$) (internal standard: TMS) (ppm):

1.16 (6H, s, 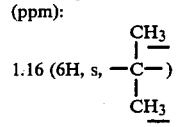)

1.2–1.8 (8H, m, 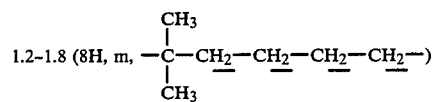)

2.23 (2H, quin, J = 6Hz, O—CH$_2$—CH$_2$—CH$_2$—O)

3.64 (3H, s, 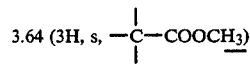)

3.86 (2H, t, J = 6Hz, 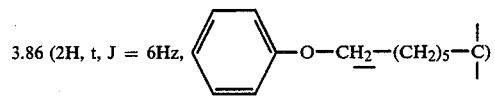)

4.10 (2H, t, J = 6Hz, 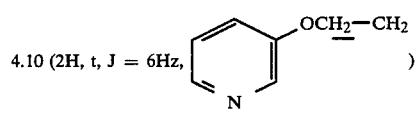)

4.18 (2H, t, J = 6Hz, 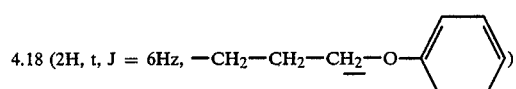)

6.79 (4H, s, 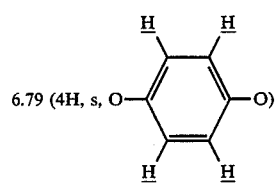)

7.16 (2H, m, 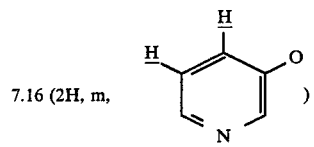)

8.16 (1H, t, J = 2Hz, 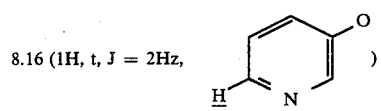)

8.28 (1H, t, J = 2Hz, 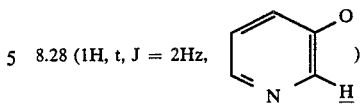)

EXAMPLE 43

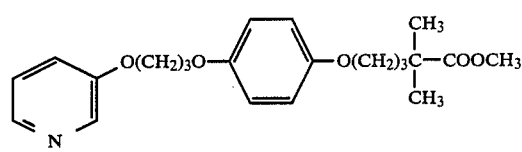

Methyl 5-[p-(3-bromopropoxy)phenoxy]-2,2-dimethylpentanoate and 3-hydroxypyridine were used as starting compounds in place of methyl 7-[p-(3-bromopropoxy)phenoxy]-2,2-dimethylheptanoate and imidazole, respectively, in EXAMPLE 33. The starting compounds were reacted and treated in a manner similar to EXAMPLE 33 to give the desired product, ethyl 2,2-dimethyl-5-[p-[3-(3-pyridyloxy)propoxy]phenoxy]pentanoate, as an oily substance.

NMR Spectrum (CDCl$_3$) (internal standard: TMS) δ (ppm):

1.22 (6H, s, 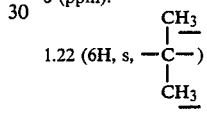)

1.5–1.8 (4H, m, 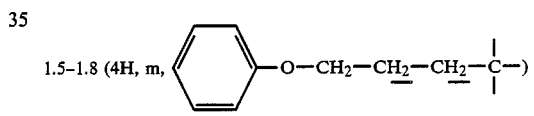)

2.26 (2H, t, J=5.8Hz, 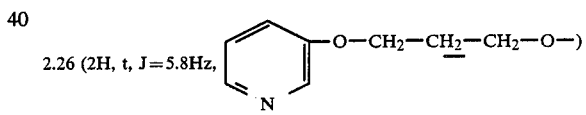)

3.68 (3H, s, —COOCH$_3$)

3.88 (2H, m, 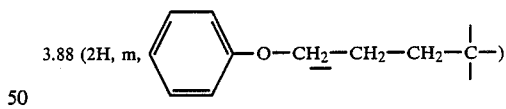)

4.12 (2H, t, J=5.8Hz, 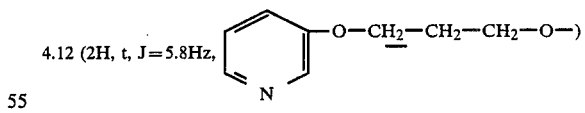)

4.22 (2H, t, J=5.8Hz, CH$_2$O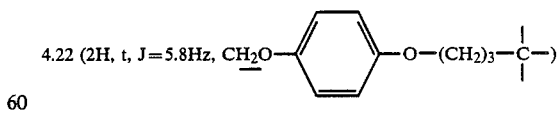)

6.84 (4H, s, 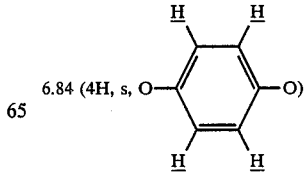)

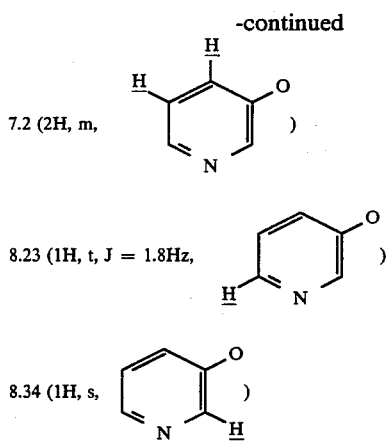

7.2 (2H, m, ...)

8.23 (1H, t, J = 1.8Hz, ...)

8.34 (1H, s, ...)

EXAMPLE 44

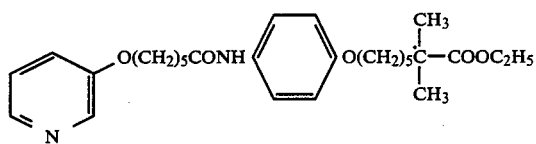

In 25 ml of methylene chloride and 0.71 g of triethyl amine was dissolved 1.47 g of 6-(3-pyridyloxy)hexanoic acid. The solution was cooled to −5° to 0° C. while stirring and 0.96 g of isobutyl chloroformate was added thereto. After stirring was continued for further 30 minutes, a solution of 2.05 g of ethyl 5-(p-aminophenoxy)-2,2-dimethylheptanoate obtained in REFERENCE EXAMPLE 8 in 15 ml of methylene chloride was dropwise added thereto. After completion of the dropwise addition, the temperature was elevated to room temperature and stirred overnight. Ice water was poured into the reaction solution and the organic layer was fractionated. The organic layer was successively washed with a saturated aqueous hydrogen sodium carbonate solution and water and then dried over anhydrous magnesium sulfate. The solvent was removed under reduced pressure and the resulting residue was subjected to silica gel column chromatography. The product was eluted out using a chloroform-methanol liquid mixture (40:1 in a volume ratio). The solvent was removed by distillation under reduced pressure. The resulting crystals were recrystallized from a solvent mixture of n-hexane-ether to give ethyl 2,2-dimethyl-7-[p-[6-(3-pyridyloxy)hexanamido]phenoxy]hexanoate.

Melting point: 64°–66° C.

| Elemental Analysis (as $C_{28}H_{40}N_2O_5$) | | | |
|---|---|---|---|
| | C (%) | H (%) | N (%) |
| Calcd. | 69.39 | 8.32 | 5.78 |
| Found | 69.32 | 8.38 | 5.75 |

EXAMPLE 45

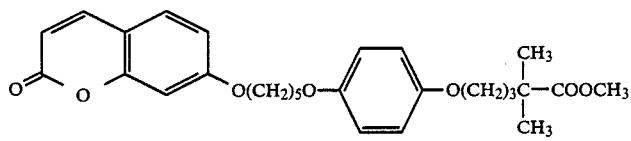

Methyl 5-[p-(5-bromopentyloxy)phenoxy]-2,2-dimethylpentanoate obtained in REFERENCE EXAMPLE 7 and 7-hydroxycoumarin were used as starting compounds in place of methyl 7-[p-(3-bromopropoxy)phenoxy]-2,2-dimethylheptanoate and imidazole, respectively, in EXAMPLE 33. The starting compounds were reacted and treated in a manner similar to EXAMPLE 33 to give the desired product, methyl 5-[p-[5-(2-chromenon-7-yloxy)pentyloxy]phenoxy]-2,2-dimethylpentanoate.

Melting point: 100°–101° C.

| Elemental Analysis: (as $C_{28}H_{34}O_7$) | | |
|---|---|---|
| | C (%) | H (%) |
| Calcd. | 69.69 | 7.10 |
| Found | 69.46 | 7.10 |

EXAMPLE 46

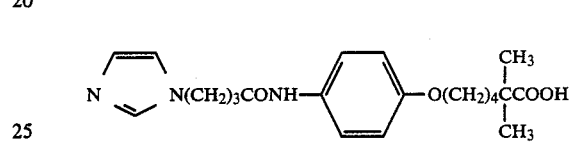

1.0 g of Ethyl-6-[p-[4-(1-imidazolyl)-butyramido]phenoxy]-2,2-dimethylhexanoate obtained from EXAMPLE 35 was stirred in 10 ml of methanol and 10 ml of 1N-aqueous sodium hydroxide solution at 40° C. for 16 hours. Ethanol was removed from the reaction mixture. The resulting mixture was washed with chloroform and then neutralized with 10 ml of 1N-aqueous hydrochloric acid solution. The precipitated crystals were collected by filtration, and recrystallized from 2-propanol to give 6-[p-[4-(1-imidazolyl)butyramido]phenoxy]-2,2-dimethyl hexanoic acid, as white crystals.

Melting point 149.5°–150.5° C.

| Elemental Analysis (for $C_{21}H_{29}N_3O_4$) | | | |
|---|---|---|---|
| | C (%) | H (%) | N (%) |
| Calculated | 65.10 | 7.54 | 10.84 |
| Found | 64.97 | 7.77 | 10.87 |

What is claimed is:

1. A phenoxy compound having the formula (I):

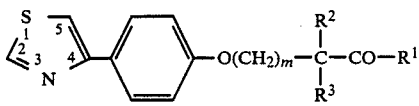

wherein $R^1$ is a hydroxyl group, amino or lower alkoxy group; $R^2$ and $R^3$, which may be the same or different, each is a hydrogen atom or $C_{1-3}$ alkyl group; and wherein the thiazolyl group can be unsubstituted, or substituted at the 2-position by lower alkyl group or amino group optionally substituted with lower alkyl group, phenyl group, cyclohexylcarbamoyl group or imidazolyl lower alkanoyl group; or substituted at the 5-position by lower alkyl group; and m is 0 or an integer of 1 to 6 pharmaceutically acceptable salts thereof.

2. The phenoxy compound of claim 1 wherein $R^1$ is lower alkoxy group and $R^2$ and $R^3$ are $C_{1-3}$ alkyl groups.

3. Ethyl 5-[p-(2-methyl-4 thiazolyl)phenoxy]-2,2-dimethylpentanoate.

4. Ethyl 5-[p-(2-amino-4-thiazolyl)phenoxy]-2,2-dimethylpentanoate.

5. Ethyl 2,2-dimethyl-5-[p-(2-methylamino-4-thiazolyl)phenoxy] pentanoate.

6. Ethyl 2,2-dimethyl-5-[p-(2-phenylamino-4-thiazolyl)phenoxy]pentanoate.

7. Ethyl 2,2-dimethyl-7-[p-(2,5-dimethyl-4-thiazolyl)phenoxy]heptanate.

8. Ethyl 7-[p-[2-(cyclohexylureido)-4-thiazolyl]phenoxy]-2,2-dimethylheptanoate.

9. Ethyl 7-[p-(2-[4-(1-imidazoyl)butylamido]-4-thiazolyl]phenoxy]-2,2-dimethyl-heptanoate.

10. 2,2-dimethyl-5-[p-(2-methyl-4-thiazolyl)phenoxy] pentanoic acid.

* * * * *